US012665094B2

(12) United States Patent
Schroeter et al.

(10) Patent No.: US 12,665,094 B2
(45) Date of Patent: Jun. 23, 2026

(54) CAUSAL INFERENCE-BASED INVESTIGATION OF ANTIMICROBIAL RESISTANCE

(71) Applicant: 342022, Inc., Newcastle, WA (US)

(72) Inventors: John Schroeter, Bainbridge Island, WA (US); Frederic L. Sax, Estero, FL (US)

(73) Assignee: 342022, Inc., Newcastle, WA (US)

( * ) Notice: Subject to any disclaimer, the term of this patent is extended or adjusted under 35 U.S.C. 154(b) by 0 days.

(21) Appl. No.: 18/626,149

(22) Filed: Apr. 3, 2024

(65) Prior Publication Data

US 2024/0331880 A1 Oct. 3, 2024

Related U.S. Application Data

(60) Provisional application No. 63/456,725, filed on Apr. 3, 2023.

(51) Int. Cl.
*G16H 70/40* (2018.01)
*G16H 10/20* (2018.01)
*G16H 10/60* (2018.01)

(52) U.S. Cl.
CPC .............. *G16H 70/40* (2018.01); *G16H 10/20* (2018.01); *G16H 10/60* (2018.01)

(58) Field of Classification Search
CPC ......... G16H 70/40; G16H 10/20; G16H 10/60
See application file for complete search history.

(56) References Cited

U.S. PATENT DOCUMENTS

| | | | |
|---|---|---|---|
| 10,496,678 | B1 | 12/2019 | Tang |
| 10,546,245 | B2 | 1/2020 | Virkar et al. |
| 10,977,580 | B1 | 4/2021 | Florez Choque |
| 11,055,891 | B1 | 7/2021 | Ofek et al. |

(Continued)

FOREIGN PATENT DOCUMENTS

| | | | | |
|---|---|---|---|---|
| JP | 2023508466 A | * | 3/2023 | ............. A61K 35/76 |
| KR | 20110003352 A | | 1/2011 | |

(Continued)

OTHER PUBLICATIONS

Mirzaei M, Furxhi I, Murphy F, Mullins M. A Machine Learning Tool to Predict the Antibacterial Capacity of Nanoparticles. Nanomaterials (Basel). Jul. 7, 2021;11(7):1774. doi: 10.3390/nano11071774. PMID: 34361160; PMCID: PMC8308172 (Year: 2021).*

(Continued)

*Primary Examiner* — Sheetal R Paulson
(74) *Attorney, Agent, or Firm* — Conley Rose, P.C.

(57) ABSTRACT

A method and system perform causal analysis on data relating to Anti-Microbial Resistant (AMR) bacteria, including receiving patient data, clinical trial data, and kinetic model of bacteria data, wherein the patient data relates to instances of AMR infections, converting the patient data, clinical trial data, and kinetic model of bacteria data into a normalized attribute form, the form being a vector format including at least a model portion for at least kinetic model data, an experiment portion for at least data describing an experiment in a clinical trial, and a data portion for at least patient data and clinical trial experimental result data, and loading the data converted into normalized attribute form into a clinical trial database.

16 Claims, 13 Drawing Sheets

100

(56)                References Cited

U.S. PATENT DOCUMENTS

| | | | |
|---|---|---|---|
| 11,450,412 | B1 | 9/2022 | Mohiuddin et al. |
| 11,790,268 | B1 | 10/2023 | Wick et al. |
| 11,804,282 | B1 | 10/2023 | Aravamudan et al. |
| 12,208,521 | B1 | 1/2025 | Puranic et al. |
| 2002/0169730 | A1 | 11/2002 | Lazaridis |
| 2010/0299335 | A1 | 11/2010 | Gopalakrishnan et al. |
| 2011/0109435 | A1 | 5/2011 | Bickel et al. |
| 2013/0238642 | A1 | 9/2013 | Clayton et al. |
| 2014/0244631 | A1 | 8/2014 | Arthur et al. |
| 2015/0286802 | A1 | 10/2015 | Kansara |
| 2016/0065597 | A1 | 3/2016 | Nguyen et al. |
| 2016/0132787 | A1 | 5/2016 | Drevo et al. |
| 2016/0253480 | A1 | 9/2016 | Comish |
| 2016/0321407 | A1 | 11/2016 | Muñoz-Jiménez et al. |
| 2018/0096105 | A1 | 4/2018 | Bleicher et al. |
| 2018/0107763 | A1 | 4/2018 | Chen et al. |
| 2019/0361908 | A1 | 11/2019 | Lee et al. |
| 2021/0257049 | A1 | 8/2021 | Abeliuk et al. |
| 2021/0288925 | A1 | 9/2021 | Tagra et al. |
| 2021/0366581 | A1 | 11/2021 | Lee et al. |
| 2022/0261538 | A1 | 8/2022 | Berns et al. |
| 2022/0365926 | A1 | 11/2022 | Iliev et al. |

FOREIGN PATENT DOCUMENTS

| | | |
|---|---|---|
| KR | 20120093972 A | 8/2012 |
| KR | 20200054203 A | 5/2020 |
| WO | WO-2019022779 A1 * | 1/2019 ............ G06N 3/045 |
| WO | 2021186196 A1 | 9/2021 |

OTHER PUBLICATIONS

International Application No. PCT/US2023/033751, International Search Report and Written Opinion mailed Jan. 22, 2024, 11 pages.

International Application No. PCT/US2023/033752, International Search Report and Written Opinion mailed Jan. 22, 2024, 9 pages.

Luo, Gang and John Schroeter. Automatic and Transparent Machine Learning. The New Popular Electronics, vol. 1, No. 1 (Dec. 10, 2017), pp. 198-206 [retrieved on Sep. 15, 2022]. Retrieved from the Internet: https://popularelectronics.technicacuriosa.com/2017/12/10/popular-electronics.

International Application No. PCT/US2024/022889, International Search Report and Written Opinion mailed Jul. 16, 2024, 17 pages.

U.S. Appl. No. 18/372,589, Office Action mailed Apr. 18, 2025, 36 pages.

U.S. Appl. No. 18/372,589, Office Action mailed Sep. 23, 2024, 30 pages.

U.S. Appl. No. 18/372,594, Office Action mailed Apr. 2, 2026, 14 pages.

* cited by examiner

100

200

400

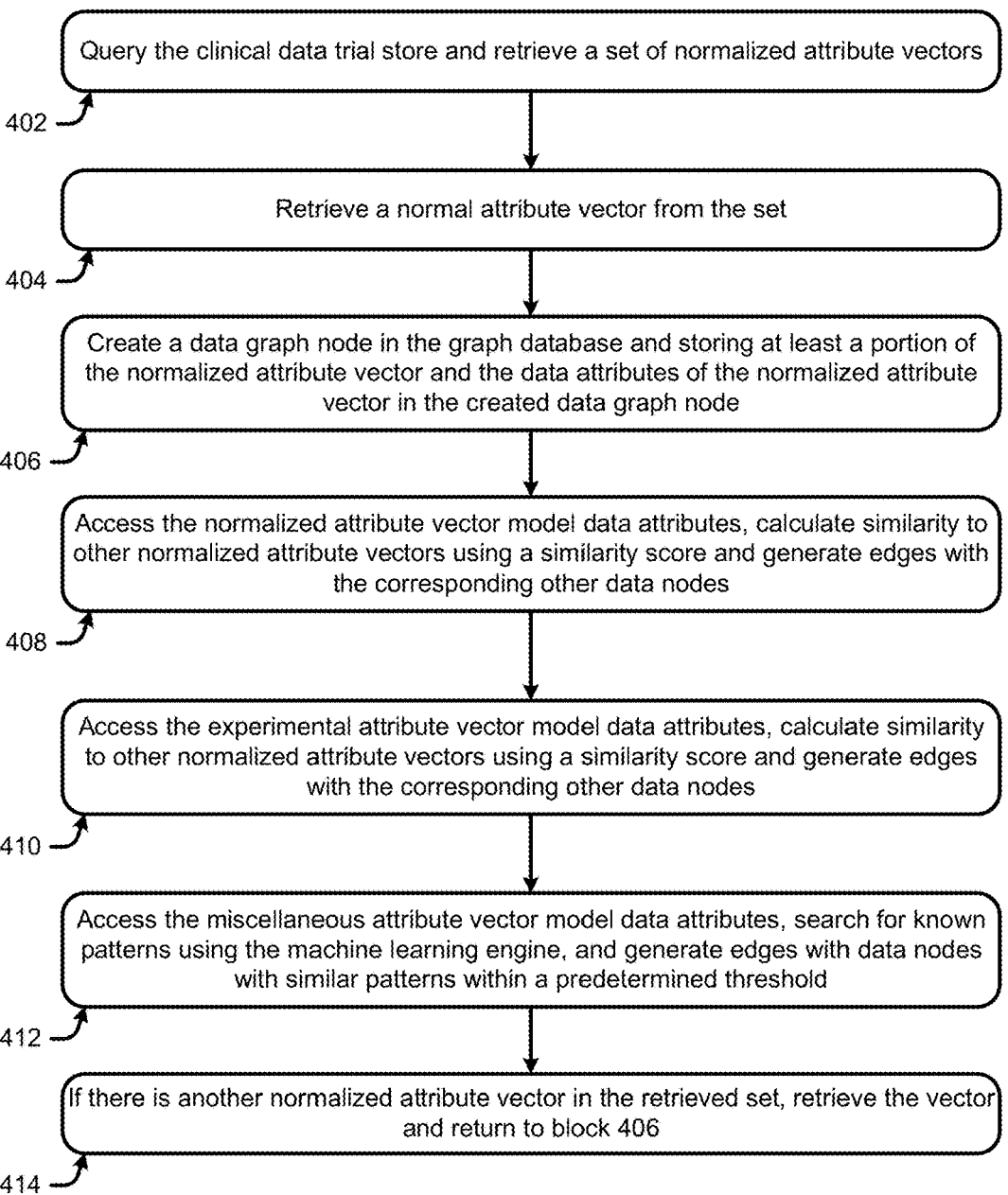

402 — Query the clinical data trial store and retrieve a set of normalized attribute vectors 404 — Retrieve a normal attribute vector from the set 406 — Create a data graph node in the graph database and storing at least a portion of the normalized attribute vector and the data attributes of the normalized attribute vector in the created data graph node 408 — Access the normalized attribute vector model data attributes, calculate similarity to other normalized attribute vectors using a similarity score and generate edges with the corresponding other data nodes 410 — Access the experimental attribute vector model data attributes, calculate similarity to other normalized attribute vectors using a similarity score and generate edges with the corresponding other data nodes 412 — Access the miscellaneous attribute vector model data attributes, search for known patterns using the machine learning engine, and generate edges with data nodes with similar patterns within a predetermined threshold 414 — If there is another normalized attribute vector in the retrieved set, retrieve the vector and return to block 406

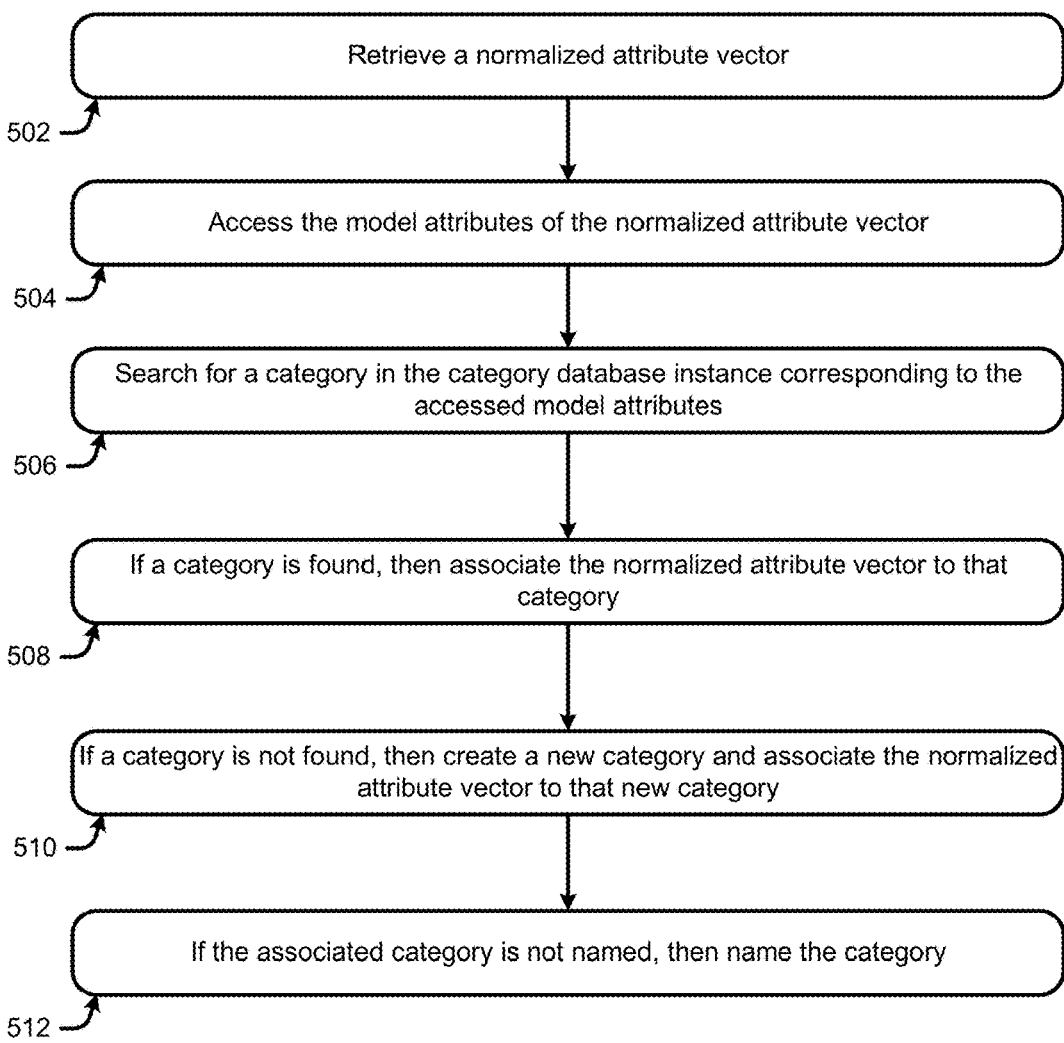

Retrieve a normalized attribute vector

502

Access the model attributes of the normalized attribute vector

504

Search for a category in the category database instance corresponding to the accessed model attributes

506

If a category is found, then associate the normalized attribute vector to that category

508

If a category is not found, then create a new category and associate the normalized attribute vector to that new category

510

If the associated category is not named, then name the category

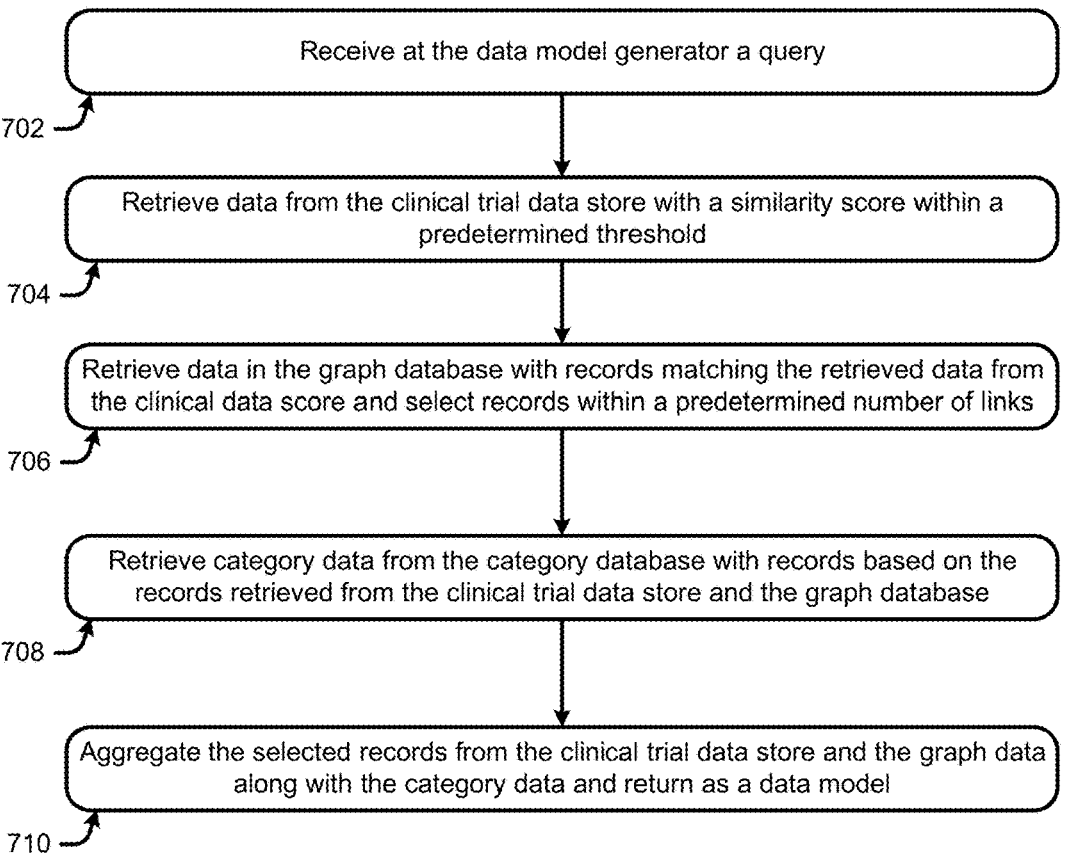

702

704

706

708

710

Receive at the data model generator a query

Retrieve data from the clinical trial data store with a similarity score within a predetermined threshold Retrieve data in the graph database with records matching the retrieved data from the clinical data score and select records within a predetermined number of links Retrieve category data from the category database with records based on the records retrieved from the clinical trial data store and the graph database Aggregate the selected records from the clinical trial data store and the graph data along with the category data and return as a data model

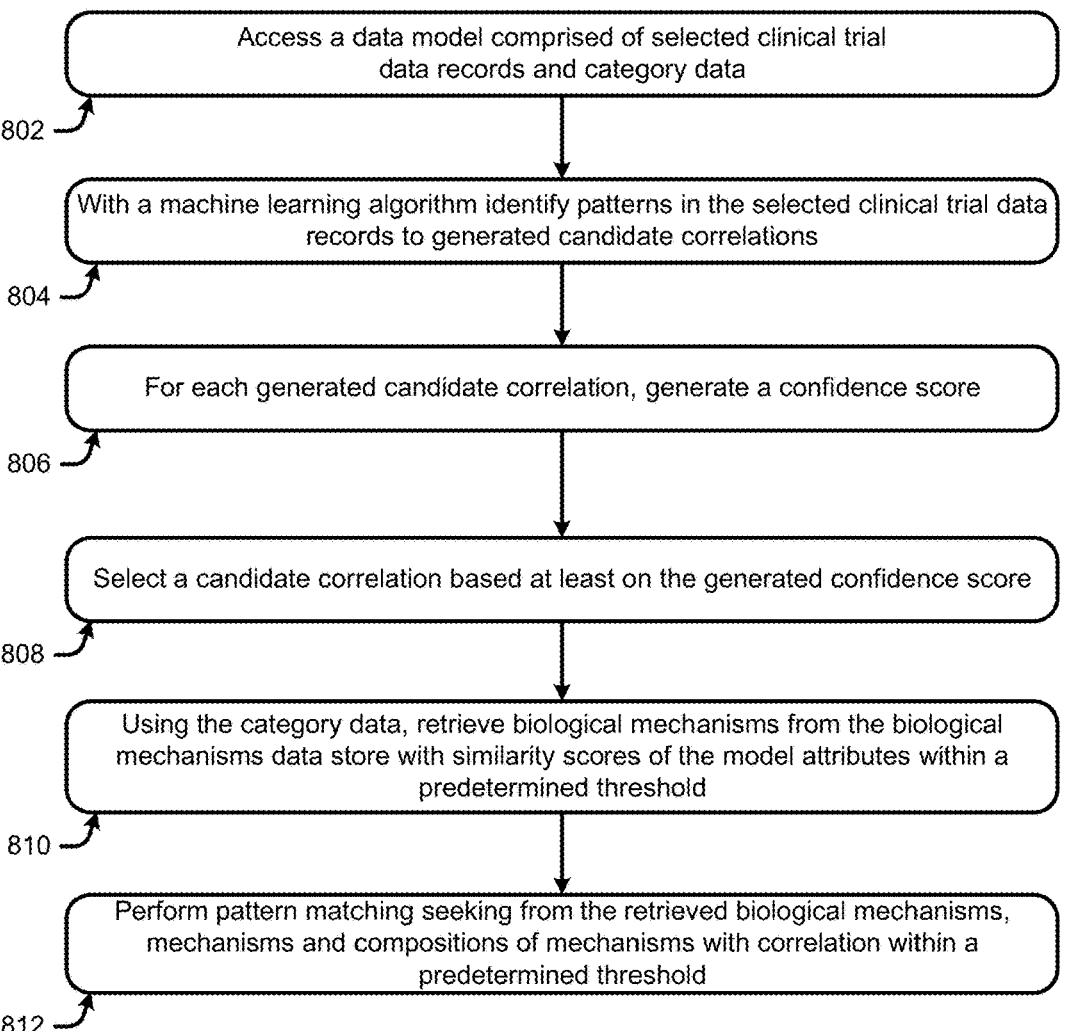

Access a data model comprised of selected clinical trial data records and category data

802

With a machine learning algorithm identify patterns in the selected clinical trial data records to generated candidate correlations

804

For each generated candidate correlation, generate a confidence score

806

Select a candidate correlation based at least on the generated confidence score

808

Using the category data, retrieve biological mechanisms from the biological mechanisms data store with similarity scores of the model attributes within a predetermined threshold

810

Perform pattern matching seeking from the retrieved biological mechanisms, mechanisms and compositions of mechanisms with correlation within a predetermined threshold

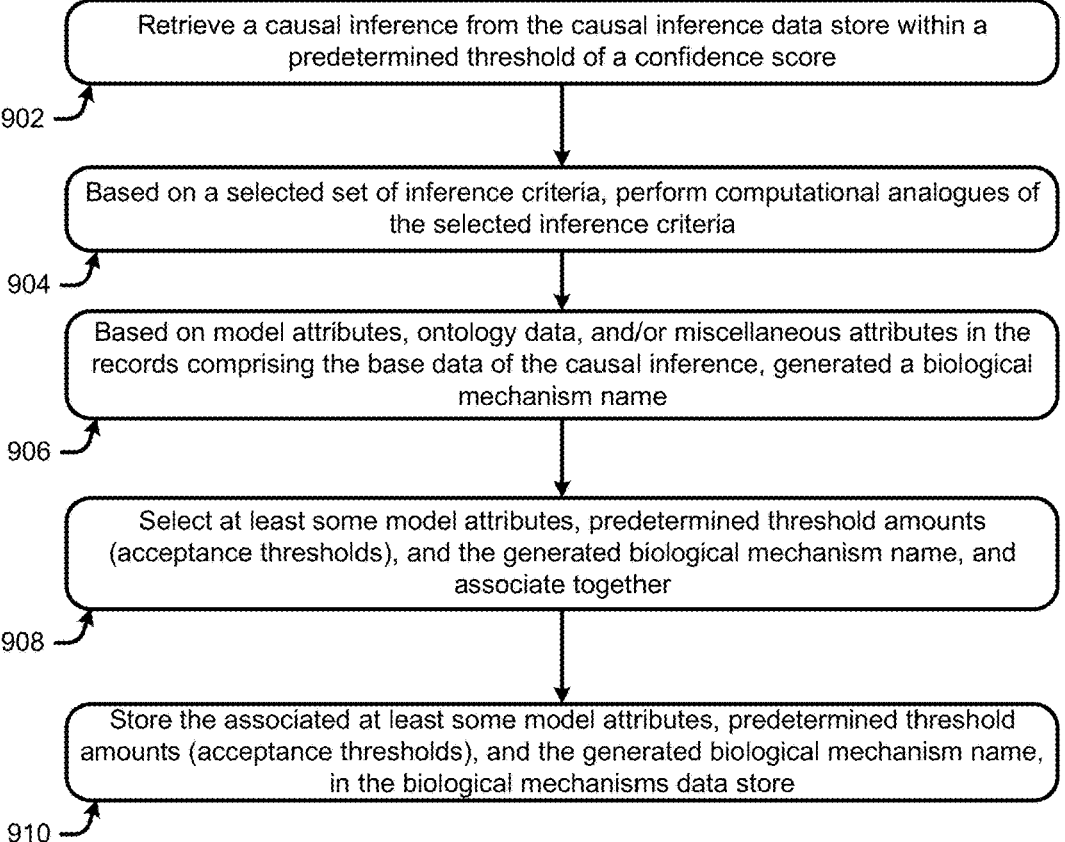

Retrieve a causal inference from the causal inference data store within a predetermined threshold of a confidence score

902

Based on a selected set of inference criteria, perform computational analogues of the selected inference criteria

904

Based on model attributes, ontology data, and/or miscellaneous attributes in the records comprising the base data of the causal inference, generated a biological mechanism name

906

Select at least some model attributes, predetermined threshold amounts (acceptance thresholds), and the generated biological mechanism name, and associate together

908

Store the associated at least some model attributes, predetermined threshold amounts (acceptance thresholds), and the generated biological mechanism name, in the biological mechanisms data store

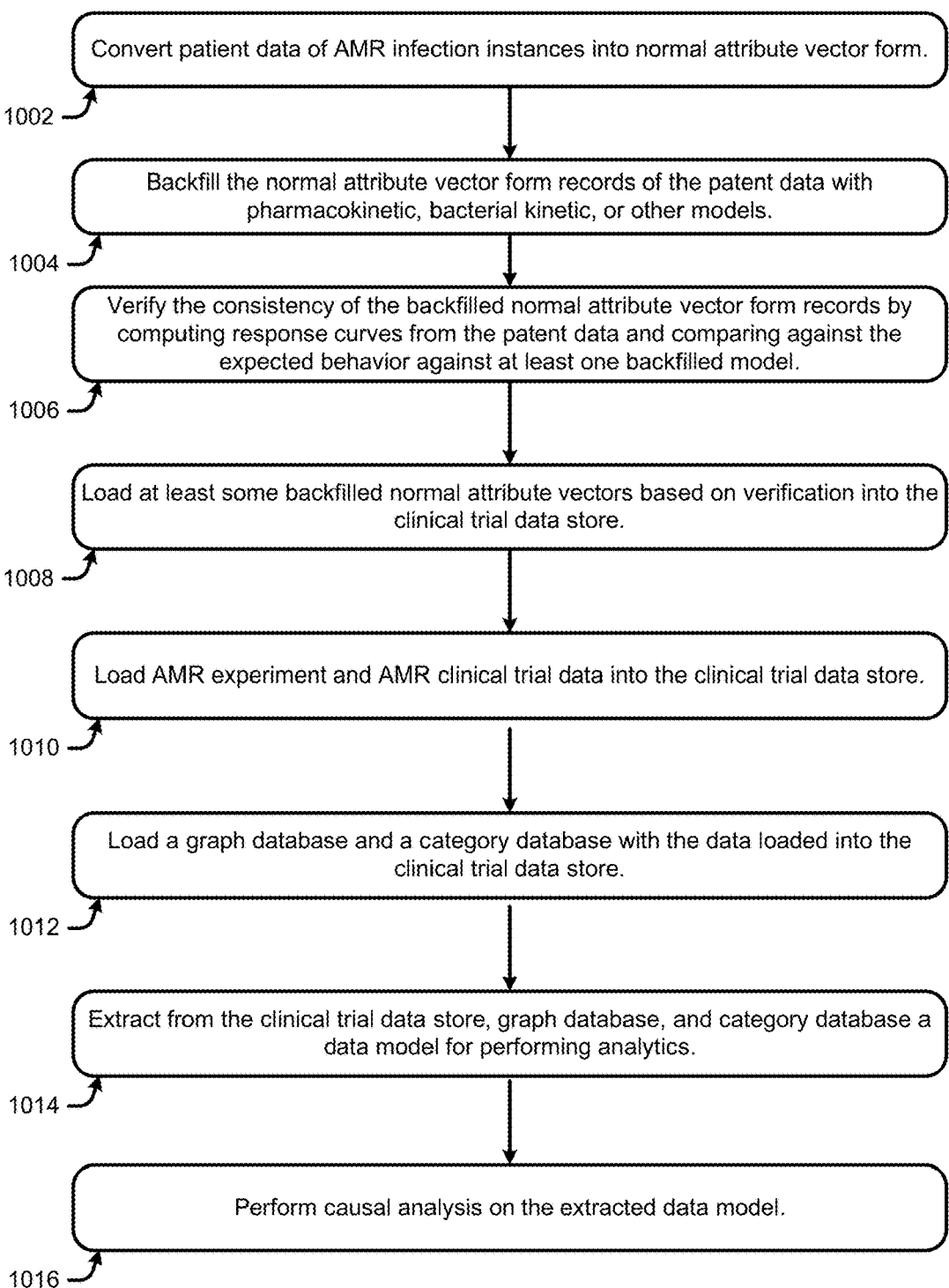

1002 —

Convert patient data of AMR infection instances into normal attribute vector form.

1004 —

Backfill the normal attribute vector form records of the patent data with pharmacokinetic, bacterial kinetic, or other models.

1006 —

Verify the consistency of the backfilled normal attribute vector form records by computing response curves from the patent data and comparing against the expected behavior against at least one backfilled model.

1008 —

Load at least some backfilled normal attribute vectors based on verification into the clinical trial data store.

1010 —

Load AMR experiment and AMR clinical trial data into the clinical trial data store.

1012 —

Load a graph database and a category database with the data loaded into the clinical trial data store.

1014 —

Extract from the clinical trial data store, graph database, and category database a data model for performing analytics.

1016 —

Perform causal analysis on the extracted data model.

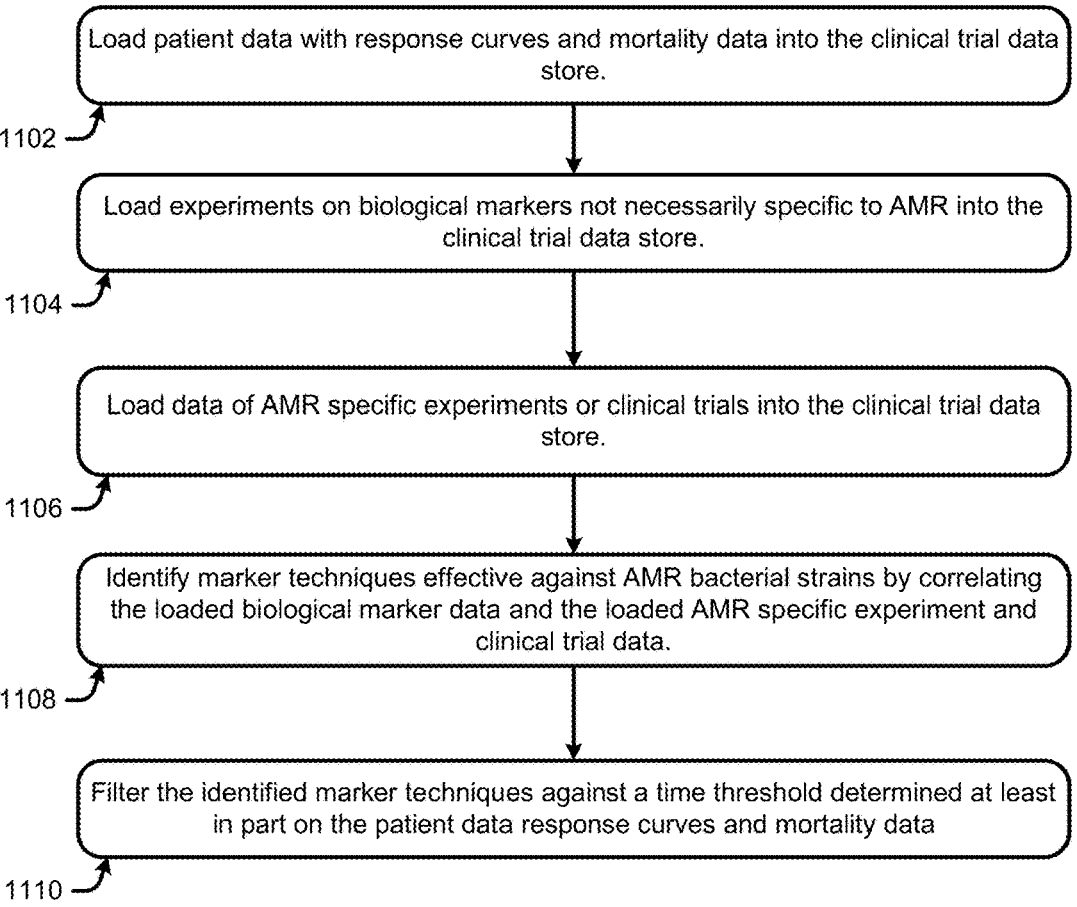

Load patient data with response curves and mortality data into the clinical trial data store.

1102

Load experiments on biological markers not necessarily specific to AMR into the clinical trial data store.

1104

Load data of AMR specific experiments or clinical trials into the clinical trial data store.

1106

Identify marker techniques effective against AMR bacterial strains by correlating the loaded biological marker data and the loaded AMR specific experiment and clinical trial data.

1108

Filter the identified marker techniques against a time threshold determined at least in part on the patient data response curves and mortality data

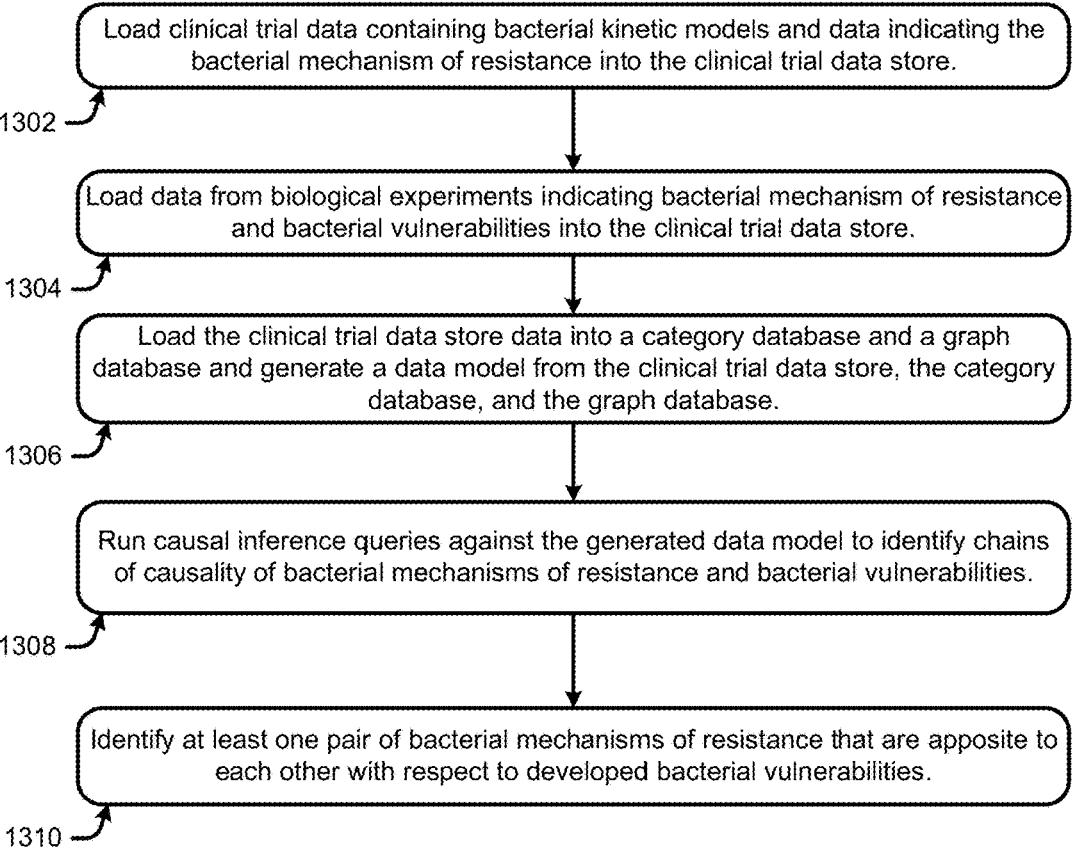

1302

Load clinical trial data containing bacterial kinetic models and data indicating the bacterial mechanism of resistance into the clinical trial data store.

1304

Load data from biological experiments indicating bacterial mechanism of resistance and bacterial vulnerabilities into the clinical trial data store.

1306

Load the clinical trial data store data into a category database and a graph database and generate a data model from the clinical trial data store, the category database, and the graph database.

1308

Run causal inference queries against the generated data model to identify chains of causality of bacterial mechanisms of resistance and bacterial vulnerabilities.

1310

Identify at least one pair of bacterial mechanisms of resistance that are apposite to each other with respect to developed bacterial vulnerabilities.

Figure 13

CAUSAL INFERENCE-BASED INVESTIGATION OF ANTIMICROBIAL RESISTANCE

CROSS-REFERENCE TO RELATED APPLICATION

This application claims the benefit of U.S. Provisional Application No. 63/456,725, filed Apr. 3, 2023, and titled "CAUSAL INFERENCE-BASED INVESTIGATION OF ANTIMICROBIAL RESISTANCE," which is herein incorporated by reference in its entirety.

BACKGROUND

At any one point in time, a huge amount of research and development is being performed at universities, public laboratories, private laboratories, commercial companies, and any number of other institutions. There is tremendous overlap between experiments and other trials being performed, but often the data from these experiments and trials are not systematically correlated or otherwise leveraged. Unless a researcher affirmatively does so, results from one trial are often not used to supplement the results of another. Accordingly, data that could strengthen the accuracy and quality of a research effort goes unleveraged.

In order for a researcher to leverage another's experimental data, that researcher not only needs to know of the other experiment, but also that the other experimental data is in fact applicable to the researcher's original experiment. Different experiments have different protocols, different models, different data formats, and the like. Accordingly, it is not a trivial exercise to determine whether the results of one experiment are applicable to another, let alone how to make those results correlate.

The scientific research involved in the discovery and testing of new medical entities is a particular instance of research for which the need to correlate data from different experiments and trials is more exigent. In the case of clinical trials, such as for drug discovery and testing, experiments are being performed on human beings, many of which have otherwise untreatable illnesses. During a trial, a patient is being told that the medication might do nothing (i.e., be placebo), make things worse (i.e., be ineffective), or maybe, just maybe, might make them better. From this context, extracting the maximum value from data goes beyond the needs of making science effective, rather it is exigent from a humanitarian perspective.

Accordingly, there is a need to discover experiments that may relate to other experiments, determine transformations, generally in the form of category theory functors and natural transformations, on how to correlate materials and data from different experiments, and to determine what conclusions may be drawn from the correlated materials and data.

One example of relating experiments to each other in order to correlate materials and data is in the area of investigating antimicrobial resistance (AMR) to drugs. AMR is the phenomenon where infection-causing bacteria develop strains resistant to antibiotic drugs. As a result, treating patients with typical drugs is ineffective where the infections are from such strains. Accordingly, there is a need not only to identify such strains, and to identify alternative therapies, but also to identify mechanisms to address the resistive adaptation of bacteria to antimicrobial drugs.

BRIEF DESCRIPTION OF THE FIGURES

The detailed description is described with reference to the accompanying figures. In the figures, the left-most digit(s) of a reference number identifies the figure in which the reference number first appears. The same reference numbers in different figures indicate similar or identical items.

FIG. 4 is a flow chart for creating a graph database from normalized attribute vectors.

FIG. 5 is a flow chart for identifying categories from normalized attribute vectors.

FIG. 7 is a flow chart for to extract data models for causal inference on category and graph data stores.

FIG. 8 is a flow chart for performing causal inference on category and graph data stores.

FIG. 9 is a flow chart for mapping causal mechanisms to causal inferences in the context of category and graph data stores.

FIG. 10 is a flow chart for causal inference-based investigation of antimicrobial resistance (AMR).

FIG. 11 is a flow chart for causal inference-based investigation of AMR with respect to detection and testing for AMR strains.

FIG. 13 is a flow chart for causal inference-based investigation of AMR with respect to testing for apposite mechanisms of resistance of AMR bacteria.

DETAILED DESCRIPTION

Figure 1:
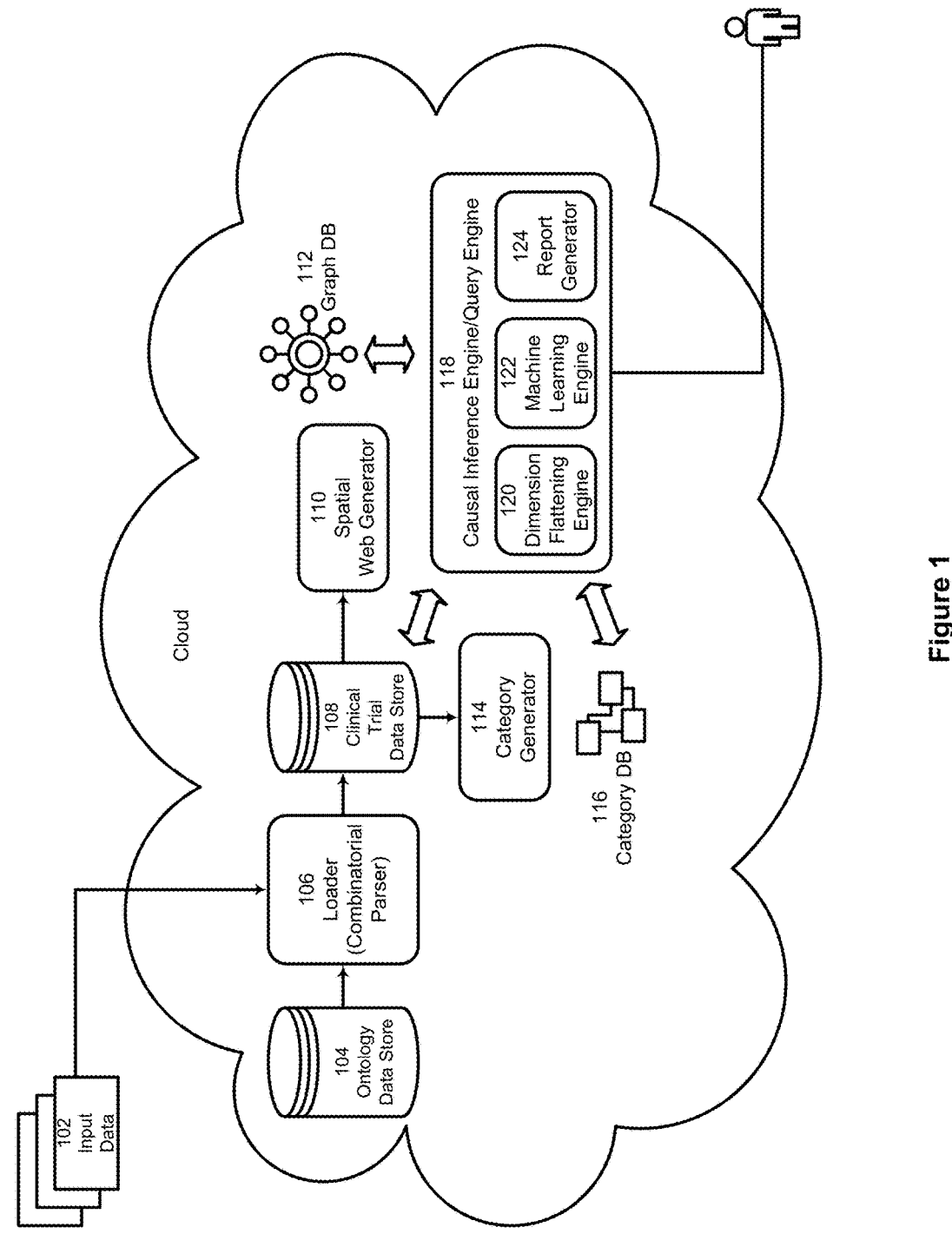
FIG. 1 is a context diagram for correlation of heterogeneous models for causal inference and for causal inference on category and graph data stores.

Context of Causal Inference-Based Investigation of Antimicrobial Resistance
The Context of Correlation of Heterogeneous Models for Causal Inference

Overview of Models

In scientific method one generally has a model to validate, where the model often has a set of parameters that represent the state of the model, and a set of rules relating those parameters. An experimenter will make a hypothesis around a model, will design an experiment on how to perturb one or more of those parameters and make observations in an attempt to verify (or intentionally contradict in order to disprove) the hypothesis, and ultimately some aspect of the model.

Models are well known in science. Parameters in mechanical physics include time, position, and mass. The state model has been extended to include non-time dependent parameters including momentum, force, energy, and work, and time dependent parameters including velocity, acceleration, and power. In some cases, parameters are statistically independent, or can be statistically dependent (i.e., derived from other parameters, e.g., velocity may be expressed as a first derivative of position, and force may be expressed as a first derivative of momentum).

Time dependent models are "dynamic" and are sometimes called "dynamical systems." The study of dynamical systems generally involves one or more ordinary differential equations (ODEs) and/or partial differential equations (PDEs).

By way of example, clinical trials for drug discovery and testing can be evaluations of dynamical systems. For example, consider pharmacokinetic models, which are models of how a substance, for example a drug, is liberated from its respective delivery system, absorbed into a subject, distributed through different tissues and organs of the subject, metabolized by the subject, eliminated from the subject, and/or the substance's general impact on the subject, such as a drug patient. Drug absorption by a person may be a function of time, and therefore dynamic. Since drug distribution, metabolism, and excretion are functions of drug absorption (and other time dependent factors), those aspect are also dynamic. As a result, many models under test in clinical trials, including pharmacokinetic models, are comprised of differential equations, many differentiated over time.

Because clinical trials are heterogeneous, that is they have different models with different underlying assumptions, it's unclear how to relate those models. For example, some pharmacokinetic models assume a single or multi-compartment model of the body, and others assume no compartments at all. In compartment models, the body is subdivided into one or more compartments, and substances are seen as propagating through those compartments. Given this degree of interactive complexity across the varying trials and research, a capability that allows correlation and causal inference across heterogeneous models would be a substantive improvement over any prior art.

Described herein are systems and methods for a causal inference engine that among other things, in at least some embodiments, makes use of category theory and dimensional flattening techniques such as with a spatial web to relate heterogeneous clinical trials. Before discussing the causal inference engine, we will discuss category theory and dimensional flattening.

Overview of Category Theory—Categories, Functors, Natural Transformations

One approach to relate what on the surface appear to be incompatible models is to make use of category theory. Category theory is a discipline of mathematics used to relate different mathematical representations. Mathematical structures, usually abstract algebraic structures, can be organized into categories. Relationships between categories are called functors, and relationships between functors are called natural transformations.

Before turning to categories with respect to causal inference, some pedagogical examples for categories may be in order. Consider two kinds of algebraic structures, first is the group (a set with a binary operation, the set supporting an identity and an inverse over the operation), and a field, (a set with two binary operations, the set supporting an identity and an inverse for each operation). A typical example of a group is the set of integers over addition (the number zero being the identity and subtraction being the inverse). A typical example of a field is the set of real numbers over addition and multiplication. The real numbers support addition in the same way integers do, and the real numbers support multiplication (the number one being the identity and division being the inverse). We say that integers over addition is an object in the category of Groups. Similarly, we say that reals over addition and multiplication is an object in the category of Fields.

The consequence is that two objects being in the same category suggests that a transformation exists to map objects from one object to the other object in a property-preserving way.

In general, mappings are not guaranteed to preserve all properties. For example, a scaling matrix transformation of two-dimensional shape preserves angles but not necessarily distances. It is of interest to identify what properties are indeed preserved across mappings. For example, if a first pharmacokinetic model belongs to a first category, and a second pharmacokinetic model belongs to a second category, those models by definition are mathematically heterogeneous. The ability to correlate those two heterogeneous models relies on the existence of mappings that preserve the properties of those models that experimenters are measuring.

An example is mathematical composition. Recall from algebra that composition of functions involves taking two functions and creating a third function by chaining those two functions. By way of example, within R→R functions (real numbers to real numbers), f(x) and g(x), h(x)=f(g(x)) is an example of composition of functions. Generalizing to category theory, mappings can be composed in the same way, and have identities and are associative.

Note that computer programming can be modeled as a series of compositions. Indeed, the functional programming paradigm is generally performed as a series of compositions and recursions. The consequence is that there are categories called monads that support such chaining via composition, and therefore support mathematical formalisms of programming.

Turning to applications of scientific inquiry and working with heterogeneous models, note that a first model and a second model can belong to a first category and a second category, respectively. Functors and natural transformations (described in further detail below) help identify mappings that are property-preserving and can be composed, thereby enabling operations on the two heterogeneous models despite being in different categories. In the case of clinical trials, note that pharmacokinetic models are oft characterized as a dynamic system comprised of a set of time-dependent ordinary differential equations. One can work directly with the differential equations, or one can make use of functionality as informed by monads as to what compositions can be made between the two heterogeneous models.

Functors represent mappings between categories. Note that functors can map items in a category to that same category. Alternatively, functors can map between two categories. Functors can be used as a means of property-preserving transformations between a structure in one category and a structure in another category.

The consequence is that if a first object is in one category and a second object is in another category, and a functor between the categories can be identified, this suggests that a transformation exists to map objects from the first object to the second object in a property-preserving way.

In fact, two categories C1 and C2, can be related as a form of weak equivalence, if a type of functor, called a left adjoint functor maps from C1 to C2 and another type of functor, called a right adjoint functor, maps from C2 to C1. The consequence is that objects in these two categories may be mixed and matched provided that transformations satisfying the identified adjoint functors are honored.

Functors themselves can be transformed in such a way to preserve properties. Such transformations are called natural transformations. The consequence is that functors and natural transformations may be used to identify how to construct transformations including via composition.

The foregoing is a very brief outline of category theory, and is not intended to be limiting, but rather to introduce terms used in this disclosure.

Applying Category Theory to Relate Models

Turning to the relation of models, consider where a first model used in a first experiment is in a first category, and a second model used in a second experiment is in a second category. If a functor can be identified between the two categories, then a mapping may be identified that maps elements, such as state variables, and operations within the model, of the first model to elements of the second model.

In the case of where the first category is the same category as the second category, category theory need not be used. However, for algorithms relying on category theory, the identity functor, which is a functor mapping from a category to the same category, and making no changes, may be made use of.

In the case where the first category and the second category are different, functors mapping two categories may be used to identify transformations between the first model and the second model, and to identify what properties are preserved across transformation. In this way results from a first model can be applied to a second model, even if the two models are in mathematically different structures. Where natural transformations exist between functors between the same two categories, techniques to refine transformational mappings between the two categories, such as composition.

Additionally, where adjoint functors exist between the two categories, this suggests that some well-defined subset of results from the two models may be aggregated together.

To be clear, data or results from different models need not be combined in their entirety. Rather, properties that represent model state parameters that in turn can demonstrate correlation, or preferably causation should be preserved. The notion of causal inference is the notion that a machine, in particular a computer, can look at a set of data and/or information, and determine whether a relationship between properties is causal. Note that correlation (as opposed to causation) is a mathematical relationship. If one can show that one statistical variable is a dependent variable with respect to an independent variable (i.e., the dependent variable is a function of the independent variable), one can demonstrate correlation. However, causation involves semantic analysis, that is to say there is a real-world mechanism that is in fact modeled by mathematical correlation. This involves making additional tests to demonstrate satisfaction of criteria to show that a correlation is in fact a causation as well. Causal inference is the automation of such tests.

In this way, causal inferences using data or results from different models may be identified.

Using the specific example of clinical trials as scientific research, there are at least two specific goals. The first goal is extrapolation. Frequently an earlier stage clinical trial will have a smaller sample size than a subsequent clinical trial, which in turn has a smaller sample size from release to the general public. Accordingly, an experimenter would be interested in understanding how information from a smaller sample size could be extrapolated to project and predict results on a larger sample size. Relating data from other experiments using category theory would increase the sample size and enable extrapolation.

The second goal is particularization. Where a clinical trial covers a relatively large sample size, an experimenter is interested in what would be the likely outcome on a specific individual. For example, a trial can show a result of a sample of 65+ year old non-smoking males with type two diabetes. However, the experimenter would be interested in determining the results for a specific individual, i.e., particularizing to an individual who not only is a 65+ year old non-smoking male with type two diabetes, but also is African American and has a body mass index of 26. Relating data from other experiments using category theory would increase the sample size and parameters under test and enable particularization.

The preceding example discusses particularization via a causal inference engine including via category theory and spatial web, to a particular person. Note that particularization need not be to a particular individual but generally will be to a class or subclass of patients. However, note that particularization taking to its logical conclusion is personalized medicine, that is the application of medical results customized to a specific patient. The causal inference engine may be used to create customized therapies and treatments for a specific patient in a specific state at a specific time. Thus, causal inference engine can enable personalized medicine.

Dimensional Flattening and the Spatial Web

The causal inference engine is also to make use of spatial web techniques including dimensional flattening. The spatial web is the outgrowth of graph database techniques where relations between records, represented as nodes, were stored as links, thereby creating a geometrically related set of records. One benefit of geometric relations is that the geometry could be relied on to determine possible and impossible relationships quickly, and perhaps more importantly to roughly situated related records within a predetermined set of links of one another. Congregating records within a predetermined set of links were sometimes called "clusters" and a cluster could be assigned a semantic interpretation.

Sets of clusters could be used to approximate volumetric shapes called manifolds. In mathematics, a manifold is a many dimensioned shape where the surface is generally continuous. A circle is a 2-dimensional manifold. A sphere is a 3-dimensional manifold. Manifolds can have holes, for example a torus, or donut shape, is a manifold.

In the case of graph databases, a spheroid with a number of records from a graph database defining the spheroids surface is a manifold.

Mathematical manifold theory has a number of techniques to approximate the surface of the manifold with fewer dimensions. For example, if one gets very close to the surface of a sphere, one could approximate a point on the sphere and items within a predetermined radius with a Euclidean plane. This provides techniques to simplify mathematical analysis.

One benefit is that the data from a graph is not necessarily continuous, but because local areas of a manifold based on data from the graph might be, one could still apply continuous techniques (for example calculus) on the limited local area.

Another benefit is the notion of dimensional flattening. Generally speaking, it is easier to perform mathematical operations using less dimensions. Volume calculations are more complex than surface calculations, which in turn are more complex than linear calculations. Considering that records may have a trillion attributes, each representing a dimension, reducing the number of dimensions under consideration can result in simpler math, less storage, and fewer computation resources utilized.

A Platform for Correlation of Heterogeneous Models for Causal Inference

A system and methods for a causal inference engine and surrounding infrastructure, together comprised of one or more software and hardware components described herein, are described. In the present exemplar, information around clinical trial data and experimental data for pharmaceuticals and test subjects that are not necessarily part of a formal clinical trial are received, transformed such that the data may be manipulated to find relations including causal inference relations making use of category theory and spatial web dimensional flattening techniques. The resulting transformed data, and results of the manipulated data are then queried to find causal inferences and related information. While the present discussion is around clinical trial data, it is to be noted that causal inferences may be found using the present causal inference engine for other sets of data, and the discussion around clinical trial data is not intended to be limiting. FIG. 1 is a context diagram 100 of a platform for the correlation of heterogeneous models for causal inference.

The causal inference engine receives input data 102 in the form of a model, and of resulting data, i.e., data showing the results of trial runs on subjects. In the case of clinical data, the model is usually in the form of a pharmacokinetic model, generally a mathematical dynamical system comprised of a set of differential equations. The resulting data are trial runs comprised of the vital statistics of various subjects, human or otherwise, showing doses and fidelity to the pharmacokinetic model. Generally, there will also be natural language notes providing context for results in general or for specific trial runs. In other cases, the data might be non-clinical trial data and may describe chemical or pharmacological phenomena.

Because different input data 102 are expected to have different models and different results, it is expected that the input data 102 will also be in different formats. However, the input data 102 needs to be converted into a standard format, which creates a data vector called a "normalized attribute vector." The normalized attribute vector may be thought of as a template or a nil vector (a vector whose attributes are empty (as opposed to zero)). In this way, the converted data may be mixed and matched during analysis in a consistent and controlled fashion.

Each incoming input data 102 file is expected to have a set of attributes. If one takes all the unique attributes of all the input data 102 files, one can store these attributes into an ontology store 104. In some examples, the ontology store 104 may be a relational database. The ontology store 104 then identifies unique attributes, and where attributes are duplicative, the ontology store 104 contains synonyms, that is corresponding names for the same attribute across different formats. The ontology store 104 may also store standardized field definitions, including type, and amount of memory. Examples of field definitions include varchar (20) (a variable length character string of up to 20 characters), date/time, integer, floating point number, and Boolean.

The input data 102 is accordingly received by a loader 106 software component. The loader 106 may comprise a multi-format parser, in some cases a combinatorial parser, and access the ontology store 104. Based on the ontology store, the normalized attribute vector for each trial data record is created using at least three sections, the first being a reference for the model of data, the second being attributes about the clinical trial such as date, source, and point of contact, and the third being the trial data itself in the form of a set of attributes normalized according to the ontology store 104.

The combinatorial parser may be implemented in conjunction with a machine learning/cognitive learning routine including for example large language models. Specifically, an artificial intelligence agent can review an input document such as a clinical trial report, an using input from a large language model that has been trained on interpretation of input documents, identify the sections of the input document to extract information from for a normalized attribute vector, interpret those sections, and output a normalized attribute vector, or a data file in a format such as JSON that can be loaded into a normalized attribute vector.

Note that several software components described herein may be depicted in FIG. 1 as software services and/or microservices resident in the cloud. However, this is not to foreclose other embodiments where software components are hosted wholly or in part on servers, discrete computers, or microprocessor chips. Alternative hosting is described in additional detail with respect to FIG. 2.

In some examples, the loader 106 then stores the records transformed into normalized attribute record format into a clinical trial data store 108. Although the records may have been originally in heterogeneous formats because all of the original records have now been converted into the same format as normalized attribute vectors, the clinical trial data store 108 is now in a state to be analyzed regardless of source.

The clinical trial data store 108 may be analyzed via spatial web analytics. In some examples, a spatial web generator 110 software component may load the data in the clinical trial data store 108 into a graph database 112 (sometimes called a spatial web database). The spatial web generator 110 takes each record in normalized attribute vector format and accesses the model and clinical trial portions to generate connections in the graph web database 112 between the records. An example of populating the graph database 112 as performed by the spatial web generator 110 is described in further detail with respect to FIG. 4 below.

Data in the clinical trial data store 108 may also be analyzed from a category theory perspective. Category generator 114 is a software component that takes each record in normalized attribute vector format and accesses its model portions to identify the mathematical properties of the model used. To be clear, a category need not be a set of instances of the same model. Rather, a category instance may be the definition of a type of mathematical representation (here a model), where the mathematical operations are similar, such that functors and natural transformations may be identified. In practice, most models will be some sort of monoidal category. An example category generator 114 is described in further detail with respect to FIG. 5 below.

Upon identifying categories of the models, the category generator 114 may store the identified categories into a category database 116. Along with identified categories, functors and natural transformations identified by the category generator are also stored in category database 116. In some cases, categories, functors, and natural transformations may also be hand-entered.

Once the data from the clinical trial data store 108 is transformed into a graph database 112 and category database 116, the data may then be queried for causal inferences and other relations. This function may be performed by a causal inference engine 118 software component acting as a general query engine.

The causal inference engine 118 may be comprised of at least three software components, a dimension (or dimensional) flattening engine 120, a machine learning engine

122, and a report generator 124. The causal inference engine 118 may receive queries either programmatically or from a user and provide responses. Performance of queries is described in further detail with respect to the report generator 124 below.

The dimension flattening engine 120 may be a software component that reviews data in the graph database 112 and identifies attributes that can be eliminated for purposes of approximating analysis. It may remove attributes that are unused and identify attributes that if removed, create the least amount of change according to a predetermined optimization function.

The machine learning engine 122 may be a software component configured to analyze data in the clinical trial data store 108, the graph database 112, and/or the category database 116. The machine learning engine 122 may make use of machine learning/cognitive network analysis, for example using one or more large language models, to identify patterns. In particular, the machine learning engine 122 may be able to recognize patterns as suggested by category theory, as simplified using dimensional flattening, and to find analogous patterns between the normalized attribute vector representation in the clinical trial data store 108, the category representation in the category database 116, and the graph database 112.

The report generator 124 may be a software component that enables both predetermined and ad hoc query capability. The report generator 124 may receive queries and respond to queries either programmatically via APIs or via an interactive query tool. In some examples, the report generator 124 receives queries for either a particular clinical trial, or type of clinical trial, and can return related categories of clinical trials, related clinical trials (as suggested by categories), or amalgamations of results from related clinical trials. In this way, a user may either perform the amalgamation manually or may rely on the causal inference engine 118 to perform the amalgamation.

An Environment for Correlation of Heterogeneous Models for Causal Inference

Figure 2:
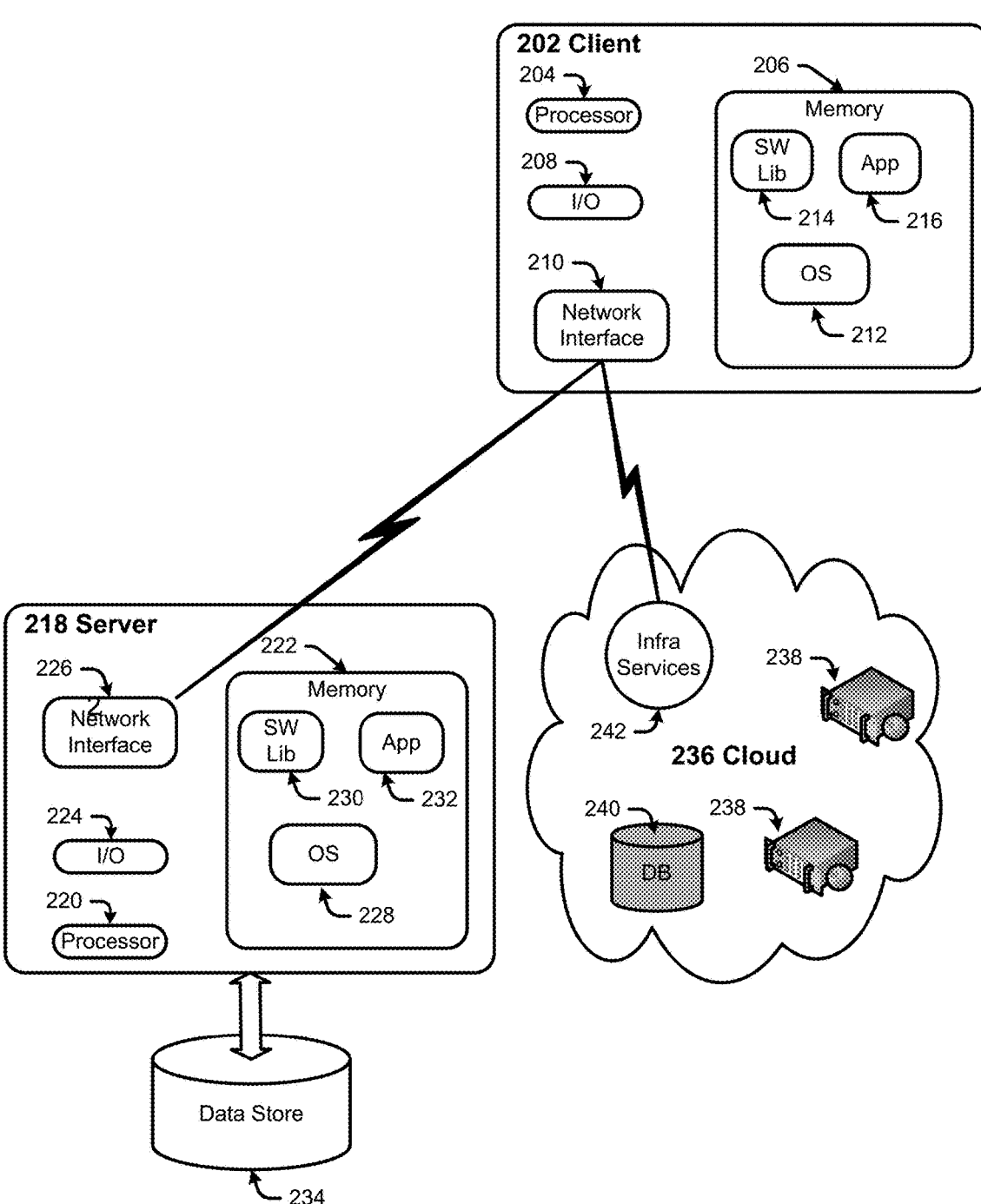
FIG. 2 is a diagram of an example environment for correlation of heterogeneous models for causal inference and for causal inference on category and graph data stores.

Before describing a causal inference engine using correlation of heterogeneous models, via FIG. 2, we describe in a diagram 200 an example hardware, software, and communications computing environment. In some examples, the functionality for correlating heterogeneous data and performing causal inference is hosted on a computing device. Example computing devices include without limitation personal computers, laptops, embedded devices, tablet computers, smart phones, and virtual machines. In many cases, computing devices are to be networked.

One computing device may be a client computing device 202. The client computing device 202 may have a processor 204 and a memory 206. The processor may be a central processing unit, a repurposed graphical processing unit, and/or a dedicated controller such as a microcontroller. The client computing device 202 may further include an input/ output (I/O) interface 208, and/or a network interface 210. The I/O interface 208 may be any controller card, such as a universal asynchronous receiver/transmitter (UART) used in conjunction with a standard I/O interface protocol such as RS-232 and/or Universal Serial Bus (USB). The network interface 210, may potentially work in concert with the I/O interface 208 and may be a network interface card supporting Ethernet and/or Wi-Fi and/or any number of other physical and/or datalink protocols.

Memory 206 is any computer-readable media which may store software components including an operating system 212, software libraries 214, and/or software applications

216. In general, a software component is a set of computer executable instructions stored together as a discrete whole. Examples of software components include binary executables such as static libraries, dynamically linked libraries, and executable programs. Other examples of software components include interpreted executables that are executed on a run time such as servlets, applets, p-Code binaries, and Java binaries. Software components may run in kernel mode and/or user mode.

Computer-readable media includes, at least, two types of computer-readable media, namely computer storage media and communications media. Computer storage media includes volatile and non-volatile, removable, and non-removable media implemented in any method or technology for storage of information such as computer readable instructions, data structures, program modules, or other data. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other non-transmission medium that can be used to store information for access by a computing device. In contrast, communication media may embody computer readable instructions, data structures, program modules, or other data in a modulated data signal, such as a carrier wave, or other transmission mechanism. As defined herein, computer storage media does not include communication media.

A server 218 is any computing device that may participate in a network. The network may be, without limitation, a local area network ("LAN"), a virtual private network ("VPN"), a cellular network, or the Internet. The server 218 may be similar to the host computer for the image capture function. It may include a processor 220, a memory 222, an input/output interface 224, and/or a network interface 228. In the memory will be an operating system 228, software libraries 230, and server-side applications 232. Server-side applications include file servers and databases including relational databases. Accordingly, the server 218 may have a data store 234 comprising one or more hard drives or other persistent storage devices.

A service on the cloud 236 may provide the services of a server 218. In general, servers may either be a physical dedicated server, or may be embodied in a virtual machine. In the latter case, the cloud 236 may represent a plurality of disaggregated servers which provide virtual application server 238 functionality and virtual storage/database 240 functionality. The disaggregated servers are physical computer servers, which may have a processor, a memory, an I/O interface and/or a network interface. The features and variations of the processor, the memory, the I/O interface and the network interface are substantially similar to those described for the server 218. Differences may be where the disaggregated servers are optimized for throughput and/or for disaggregation.

Cloud 236 services 238 and 240 may be made accessible via an integrated cloud infrastructure 242. Cloud infrastructure 242 not only provides access to cloud services 238 and 240 but also to billing services and other monetization services. Cloud infrastructure 242 may provide additional service abstractions such as Platform as a Service ("PAAS"), Infrastructure as a Service ("IAAS"), and Software as a Service ("SAAS").

A Normalized Attribute Vector

Figure 3:
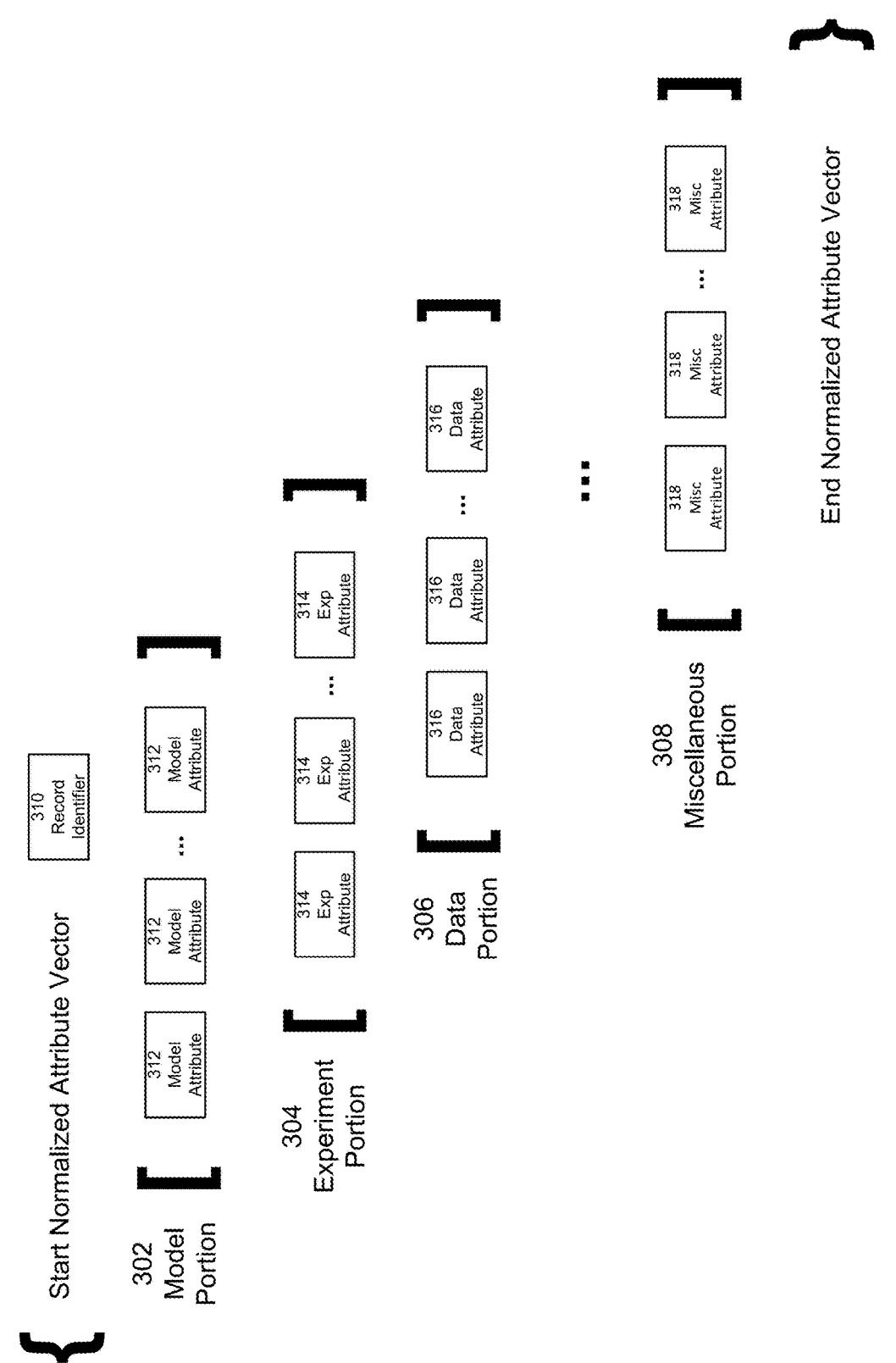
FIG. 3 is a diagram of an example normalized attribute vector.

FIG. 3 illustrates an example normalized attribute vector 300. The normalized attribute vector 300 may store a set of attributes that describe a record from an arbitrary clinical trial or experimental results. An attribute is a key-value pair where the attribute name represents the key, and some data represents the value. The data may also be a reference to a value rather than the value itself. The attribute names are taken from the data in the ontology data store 104.

The normalized attribute vector 300 is comprised of a plurality of attributes. There may be a very large set of potential attributes. In some cases, there may be trillions of attributes. However, it is not the case that all attributes will have assigned values. To organize the attributes, there are four portions of the normalized attribute vector 300. First there is a model portion 302 which contains attributes describing the mathematical or pharmacokinetic model used for the record associated with the normalized attribute vector 300. Then there is an experiment portion 304 which contains attributes describing the experiment and the circumstances of the experiment. Next there is a data portion 306 which provides values representing the experimental results of a trial or experimental run. Finally, there may be a miscellaneous portion 308, which may contain additional attributes reported.

For example, there may be a normalized attribute vector identifier attribute 310. The identifier attribute 310 may be a value guaranteed to be unique. Such a value may be generated by a sequential iterator (e.g., a monotonically increasing integer generator creating 1, 2, 3 . . . ) or by a globally unique identifier (GUID) generator.

The model portion 302 may contain enough information in the form of model attributes 312 to determine whether the model in the record corresponding to the normalized attribute vector 300 has the same mathematical characteristics of another model, and therefore should be considered in the same category. Some pharmacokinetic models are comprised of various sets of ordinary differential equations. Others make use of partial differential equations. Some models are container based and others are not. Model attributes 312 may describe these aspects and other aspects of a model (or provide references to review the model) as to enable the identification of a predetermined category, to assign the model in the record corresponding to the normalized attribute vector 300 to that category, and then to identify functors and potentially natural transformations associated with the category for application to the model in the record corresponding to the normalized attribute vector 300.

The experiment portion 304 may contain enough information in the form of experiment attributes 314 to determine patterns about ensuring the various experiments have similar design and were performed under similar circumstances. Experiment attributes 314 may identify one or more protocols (biological workflows), in the form of steps. Other experiment attributes 314 may identify labs where performed, parties involved in performance, date/time, and other environment aspects. The data in the experiment attributes 314 may enable a machine learning engine 122 to identify patterns in data. For example, a machine learning engine 122 might identify a specific lab as having particular accurate and easily reproducible results.

The data portion 306 may contain actual data results in the form of data attributes 316 for a particular trial or experimental run. The data attributes 316 may have attribute names taken from the ontology data store 104. Where a particular attribute is not used, the value may be set to "not applicable" (as opposed to zero which may be a valid value). In this way, one can identify applicable attributes during dimensional flattening.

The miscellaneous portion 308 may contain miscellaneous attributes 318 that provide additional information for context. For example, an attribute labeled "Error" may indicate that the test result was based on an erroneously executed run. Another attribute label "Comment" may be a natural language value containing contextual notes. In some cases, the machine learning engine 122 may perform natural language analysis on such natural language attribute values to detect patterns.

A Method for Correlation of Heterogeneous Models for Causal Inference—Graph Database Instance Generation FIG. 4 is a flow chart 400 that shows an example of manipulating normalized attribute vectors 300 as stored in the clinical trial data store 108. The flow chart 400 illustrates an example method for generating a graph database 112 from normalized attribute vectors 300 by the spatial web generator 110.

Turning to FIG. 4, the goal is to take a queried set of normalized attribute records and create a graph database instance stored in graph database 112. Note that graph database 112 can store multiple instances of graph databases. Here we create a new graph database instance. This involves creating data nodes and edges between the data nodes for that instance. In flow chart 400, the edges will be based on manipulation of data stored in the model attributes 302, experiment attributes 304, and miscellaneous attributes 308 of a normalized attribute vector 300.

In block 402, the clinical data trial store 108 is queried according to a set of parameters. If the clinical data trial store 108 is a relational database, with attributes representing fields, the query may be in the form of a structured query language query with parameters referring to fields. Upon execution of the query, a set of normalized attribute vectors is returned in the form of a SQL recordset.

In block 404, the SQL recordset is iterated through (for example, a cursor iterated through the records corresponding to normalized attributed vectors one by one). The record, which is comprised of a normalized attribute vector, that is pointed to by the cursor is retrieved or otherwise accessed.

In block 406, a data node in the graph database is added storing at least a portion of the normalized attribute vector 300. In actual practice, only the unique normalized attribute vector identifier 310 is stored. To access attributes of the normalized attribute vector 300, the identifier 310 is used to access attributes to the record stored in the clinical trial data store 108.

In block 408, the model data attributes 302 of the normalized attribute vector 300 just added are retrieved and compared with the model data attributes 302 of all nodes already in the graph database instance. The comparison is performed using a similarity score. If the similarity score is within a predetermined threshold, then an edge between the new node and the existing node in the graph database instance is created.

In block 410, operation may be similar as in block 408, except here the experimental data attributes 304 are accessed. As in block 408, the attributes themselves may be compared according to a similarity score and if the similarity score is within a predetermined threshold, then an edge between the new node and the existing node in the graph database instance is created.

In block 412, operation may be similar as in blocks 408 and 410, except here the miscellaneous data attributes 308 are accessed. However here, because free form natural language is used, machine learning from the machine learning engine 122 is applied to the natural language fields to identify pattern types. When comparing natural language attributes, where the identified pattern type from the machine learning engine 122 is within a predetermined threshold, then an edge between the new node and the existing node in the graph database instance is created.

In block 414, the cursor is incremented and the recordset is accessed to determine if there is another normalized attribute vector. If there is, then operation returns to block 406. Otherwise, the operation is terminated. The result is a graph database instance populated with references to the normalized attributed vectors from the recordset, and edges created based on model attributes 302, experiment attributes 304, and comment and other attributes in the miscellaneous attributes 308.

Method for Correlation of Heterogeneous Models for Causal Inference—Category Identification Turning to FIG. 5, FIG. 5 is a flow chart 500 that shows the manipulation of normalized attribute vectors 300 as stored in the clinical trial data store 108 to identify categories by the category generator 114. Note that the category database 116 stores categories, functors, and natural transformations. Note further that the category database 116 can also create different instances of category databases, each corresponding to some subset of normalized vector attributes. The goal is to take a normalized attribute vector 300 that is not associated with a category, and to either associate it with a category in the category database 116, or if an appropriate category does not exist, create one in the category database and then associate the normalized attribute vector 300 with the newly created category. For categories stored in the category database 116, each stored category may be associated with a set of model attributes that can be used to comparison purposes when determining whether a normalized attribute vector 300 should be associated with that category.

In block 502, a normalized attribute vector 300 may be retrieved. As with blocks 402 and 404, the normalized attribute vector 300 may be part of a recordset retrieved via a SQL query from the clinical trial data store 108 or may simply be a standalone record.

In block 504, the model attributes 302 of the retrieved normalized attribute vector 300 may be accessed. Since the model attributes 302 describe the mathematical and/or pharmacokinetic model used, these model attributes 302 may be used to determine a category.

In block 506, the model attributes 302 of the retrieved normalized attribute vector 300 may be compared to attributes associated to the various categories in the category database 116. If a category is found, in block 508, the normalized attribute vector 300 may be associated with the category. In practice, the category database 116 may not store the full normalized attribute vector 300, but instead only the vector identifier 310.

If a category is not found, in block 510 a new category may be created in the category database 116. As stated above, stored categories may be associated with attributes. Here the attributes associated with the new category may be based at least in part on the attributes of the normalized attribute vector 300 under analysis.

Note that the in block 510, the newly created category is not necessarily yet named. At some future time, a name may be manually added, or automatically associated via machine learning.

At the end of this process 500, the result may be a category database instance with a full set of categories, each category associated with attributes, and each category associated with at least identifiers of a set of normalized attribute vectors 300. Over time, functors and natural transformations may be identified and added to the category database 116. At that point, in conjunction with graph database 112, causal inferences on the thereby correlated heterogeneous models may be performed.

Context of Causal Inferences on Category and Graph Data Stores

Causal inferences on category and graph data stores apply to scientific research and inquiry in general. However, consider, for example the context of heterogeneous medical clinical trials. At this point, we have constructed clinical trial data store 108, category database 116, and graph database 112. The clinical trial data store 108 contains data from multiple heterogeneous clinical trials all in a normalized attribute vector formal 300. Accordingly, we are ready to identify causal inferences in the aggregated heterogeneous data. In other words, we wish to perform analysis on data to determine whether a factor causes an effect. Computational methods may show correlation but not causation Causal inference is a technique to determine whether an observed machine learning pattern represents a cause and not merely a correlation.

It is well known in scientific method that when a team of experimenters selects a model as a starting point, they will attempt to validate (or invalidate) the selected model by attempting to perturb one and only one variable in an experiment. The reason is to isolate the perturbed potential cause of observed effects in the experiment. If more than one variable is perturbed, then the experimenter is faced with determining which variable, or which combination of variables caused the observed effects.

Furthermore, it is well known that there is a difference between correlation and causation. With the former, we can only observe that a perturbed variable is statistically present whenever we observe an experimental effect. With the latter, we can show systemically how the perturbed variable is the indicator of a mechanism that creates or otherwise creates conditions for the observed experimental effect. In other words, in causation, we recognize that a statistical effect does not illustrate a causal mechanism. This is only possible with a qualitative model, not merely a quantitative model.

Consider the case of a child in child seat in the back in a car being driven by a parent. The child cannot see what the parent is doing. However, whenever the car veers right or left (i.e., the child feels the car turning), the child also hears a ticking noise coming from the parent having activated the turn signal. The child might be forgiven for thinking that the ticking sound causes the veering effect—quantitatively, The issue is that the child does not have a qualitative model of the mechanics of turning the car. The child is not aware that there are customs and regulations to enable the driver and car to safely be on the road at the same time as others, and that the signal is for the benefit of those others. The child is not aware that signaling obligations are on the driver, in this case the parent. Furthermore, the child cannot see the parent driving, and accordingly cannot see that the parent is in fact the mechanism activating a turn signal which is creating the ticking sound.

Correlation can be very persuasive, but can also be very misleading, including in careful scientific inquiry. Consider the geocentric (Earth-centric) model of the solar system promulgated by Ptolemy's Almagest. Today, with general knowledge and acceptance of the heliocentric (sun-centric) model, discussion of the geocentric model is described almost with derision verging on contempt. This is unwarranted. Ptolemy was known to be an expert and the Almagest is replete with some of the most careful and precise star charts of all time. In fact, the Almagest is still used today to determine the motion of stars over the past 2000 years.

The geocentric model required the notion of epicycles to explain planetary retrograde motion, a very unwieldy mechanism. But beyond reputation, the Almagest enabled the prediction of eclipses and occultations (events where stars, planets, and other astronomical observable bodies crossed paths). That ability made very serious scientists to have confidence in the geocentric model and epicycles, regardless of the mathematical and conceptual awkwardness. In fact, the Copernican heliocentric model proposed using perfect circles and could not predict eclipses accurately, thereby weakening the case for the heliocentric model.

The flaw was that there was no mechanism to explain why an epicycle should occur in the first place. Scientists only knew that you could get consistent, repeatable, and predictable effects. Until Newton proposed the notion of gravity, there was no basis as to why a model should be heliocentric or geocentric. And until Newton developed mechanical physics and the calculus (contemporaneously with Leibniz), and until Kepler modified the heliocentric model to use ellipses instead of circles, to enable predictions of eclipses and occultations was there a causal basis for the heliocentric model.

Turning back to our discussion of clinical trials, it is particularly important to have a causal, not merely correlative, basis for understanding the mechanisms of proposed drugs. Note that drugs may have side effects, many quite unpleasant. If the specific causal mechanisms can be identified, then side effects can also be predicted, and the drug developed can be directed towards minimizing side effects and maximizing proper targeting.

To this end, clinical trials, and medical/pharmacological research make use statistical methods such as ANOVA to identify and isolate correlations but make use of rigorous factors to determine the likelihood of causation. The starting point for such factors may be the Hill Criteria which include as its factors: (1) evaluations of strength, (2) consistency and causation, (3) specificity, (4) temporality and causation, (5) biological gradient, (6) plausibility, (7) coherence and causation, (8) experimental result, and (9) analogy. The factors are described in greater detail in Hill's 1965 paper, "The Environment and Disease, Association or Causation?" Note that the criteria have been evolved over time and are not dispositive.

The foregoing motivates the combination of category and graph databases. Machine learning and cognitive networks are inherently statistical in nature. In some instances, they can show correlation. However, categories are deterministic. If two objects are instances of the same category, we can say that those instances are the same in some well-defined, property-preserving respect. Similarly, functors and natural transformations are deterministic and are both well-defined and property-preserving. In other words, we can use categories and categorical relationships to demonstrate causation, suggested by observed correlations in graphs and machine learning, by associating a mechanic with a category/functor/natural transformation structure.

Because category theory, by definition, supports mathematical composition, we can start with simple, smaller, well understood mechanics, associate the mechanics as an interpretation of category theory artifacts, and construct more complex mechanisms using composition of those category theory artifacts. Accordingly, if we are confident in the simpler causality mechanics, then we can be confident in the compositions of those simpler mechanics in to larger and more complex causations.

Figure 6:
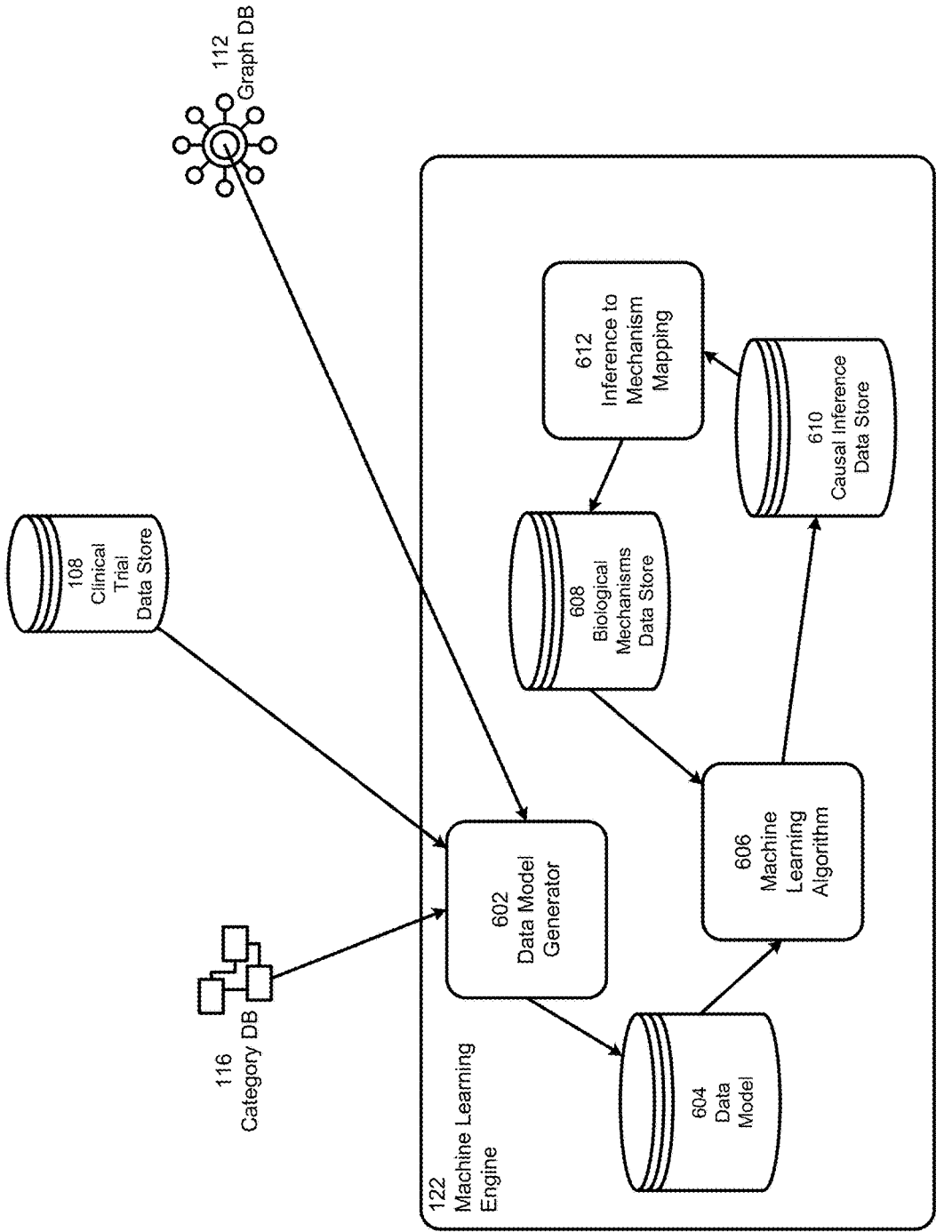
FIG. 6 is a diagram of an example environment for causal inference on category and graph data stores.

Machine Learning Configuration for Causal Inferences on Category and Graph Data Stores FIG. 6 is a diagram 600 for an example machine learning configuration for causal inferences on category and graph data stores. In some examples, the machine learning engine 122 may create data models from the category database 136 and the graph database 112 and if needed supplement the data with data directly from the clinical trial data store 108. The machine learning engine 122 may have a table of validated mechanics mapped to category theory artifacts. The machine learning engine 112 and then use this table to search for patterns that are compositions of those validated mechanics.

A query engine 118 may receive a query from a user to search for causal inferences on a set of data. The query engine 118 may interpret the received query as a search for correlations in data and furthermore to validate those compositions of validated known mechanisms. To do so, architecturally a data model generator 602 software component may convert the received query and retrieve data from the category database 116, the graph database 112, and in some cases the clinical trial data store 108, into a software data model 604. The generation of the data model is described in further detail with respect to FIG. 7.

A machine learning algorithm 606 software component may then search for various patterns correlating patterns in the clinical trial data store 108 data and the graph database 112 data. The correlated patterns are then validated by the machine learning algorithm 606 using a biological mechanisms data store 608 of validated patterns mapped to an interpretation of a known biological mechanism, i.e., a trusted causal mechanism. If the machine learning algorithm 606 can discern a mathematical category theory-based composition (or other mathematical composition) of known biological mechanisms from the biological mechanisms data store 608, then the result is returned to a causal inference data store 610. The query engine 118 may then return a result to the querying user based at least on some portion of the returned causal inference. The operation of the machine learning algorithm 606 is described in further detail with respect to FIG. 7.

In some cases, the biological mechanisms data store 608 is supplemented with new mechanisms. Where the statistical confidence of a detected causal inference exceeds a predetermined threshold, the machine learning engine 122 may be configured to promote an inferred causation in the causal inference data store 610 to a trusted and validated biological mechanism to be stored in the biological mechanisms data store 608. This function is performed by the inference to mechanism mapping 612 software component.

Note that in some cases, such as in training and tuning the inference to mechanism mapping, candidate mechanisms for promotion may be surfaced to a developer, administrator, or other user as part of training a machine learning model or developing rules for a rules engine. However, the inference to mechanism mapping software component 612 is itself implemented in a fully automated fashion making use of rules engines and/or machine learning models that would reflect choices during identifying rules for the rules engine and/or training machine learning models. The operation of the inference to mechanism mapping 612 is described in further detail in FIG. 8.

Data Model Generation

As stated above, the data model generator 602 converts queries into data models. FIG. 7 is a flow chart 700 of one embodiment of this process.

In block 702, the data model generator 602 receives a query from a user as forwarded by the query engine 118. The query may include a set of attributes normalized according to the ontology data store 104. In other words, the attributes use the same names and value rules set forth in the ontology data store 104. In this way the attributes in the query can be matched to attributes in records in normalized attribute vector 300 format.

In block 704, the data model generator 604 queries data from the clinical trial data store 108 that match the query attributes using a similarity score. Data with a similarity score within a predetermined threshold are selected.

In block 706, the data model generator 606 queries the graph database 112 for all records within the selected records from block 704. The selected records may then be supplemented or reduced based on records in the graph database 112 within a predetermined number of links. In the case that some records in the graph database 112 are within the predetermined number of links, those records are added to the selected set. Where the records are beyond the predetermined number of links within the graph database 112, those records may be retained in the selected set, or alternatively may be deleted, depending on the querying user's desired statistical confidence.

In block 708, the data model generator 602 queries the category database to retrieve at least some categories, functors, and natural transformations based on the selected records. In some examples, the selected records are associated with models as represented by their model attributes 302.

In block 710, the data model generator 602 then aggregates the final selected records and the retrieved categories, functors, and natural transformations into a data model 604. Recall that manipulations of the data are possible because all records are in normal attribute vector 300 format.

Performing Machine Learning Causal Inference

Once we have a data model 604, we can search for patterns using machine learning to determine correlations and causations. FIG. 8 is a flow chart 800 of such an example of the process.

In block 802, a machine learning algorithm 606 is applied to data model 604. The machine learning algorithm 606 may be seeking data with correlating results and is further configured to seek correlations that are compositions of biological mechanisms in the biological mechanisms data store 608.

In block 804, the machine learning algorithm 606 identifies candidate correlations. For example, the machine learning algorithm 606 may seek correlations of data based on similar data from the clinical trial data store 108 data attributes making use of various similarity scores. It also looks for patterns in graph database 112 on the basis of proximity within the graph database 112. The patterns from the clinical trial data store 108 and the patterns from the graph database 112 are then correlated. Note that the data model generator 602 created the data model 604 in a similar process. However, here because we are seeking correlations to more fine-grained predetermined thresholds.

In block 806, the machine learning algorithm 606 generates a confidence score for each identified candidate correlation. The confidence score is a function of the error calculation for the machine learning algorithm 606.

In block 808, a subset of records corresponding to a candidate correlation is selected based on the calculated confidence of the candidate correlation exceeding a predetermined threshold.

In block 810, the machine learning algorithm 606 uses categories, functors, and natural transformation in the query to retrieve biological mechanisms in the biological mechanisms data store 608 with similarity scores within a predetermined threshold. Recall that the biological mechanisms data store 608 does not merely store mathematical constructs, it also stores interpretation of those constructs as biological mechanisms that are trusted. In this way, a composition that is otherwise mathematically feasible can be rejected as not being biologically possible mechanically.

In block 812, the machine learning algorithm then performs pattern matching to seek biological mechanisms and compositions of biological mechanisms from the biological mechanisms data store 608 within a predetermined threshold.

In block 814, where the pattern matching is within a predetermined threshold, the candidate correlation is returned as a candidate causal inference and is stored in the causal inference data store 610. The query engine 118 may then return some subset of the candidate causal inferences to the user or alternatives may apply further processing such as with the inference to mechanism mapping 612.

Automated Inference to Mechanism Mapping

At this point we have a set of causal inferences stored in the causal inference data store 610. Because the causal inferences are compositions of trusted biological mechanisms in the biological mechanisms data store 608, the inferences are consistent with those mechanisms. It would be advantageous to store the inferences as a biological mechanism itself in the biological mechanisms data store 608. In this way, the computation expended to identify the pattern need not be expended again and again and can be used to discover further patterns and mechanisms. However, the causal inferences are not yet validated and therefore are not yet to be trusted. Furthermore, a biological mechanism has not necessarily been identified to associate as an interpretation of the underlying mathematical structure. FIG. 9 is a flow chart 900 of a process to validate causal inferences and therefore store in the biological mechanisms data store.

In block 902, the inference to mechanism mapping 612 software component retrieves a causal inference from the causal inference data store 610 based at least on a confidence score. In general, the inference to mechanism mapping 612 seeks relative high confidences.

In block 904, the inference to mechanism mapping applies a computational mapping of a predetermined set of causality criteria.

Example computational mapping include performing computations analogues of the Hill Criteria mentioned above. For example, regarding the Hill Criterion of plausibility, where compositions are mathematically but not biologically possible, candidate causal inferences may be eliminated. Similarly, the Hill Criterion of biological gradient of the records may be computed, and curve fitting algorithms applied to determine a confidence score. Where the confidence score is within a predetermined threshold, the candidate causal inference may be accepted for storage in the biological mechanisms data store.

In block 906, candidate names for the biological mechanism may be generated by the inference to mechanism mapping. In some examples, machine learning may be applied to the names of the models, data in the ontology data store, but also parsed text in the miscellaneous attributes 308. In some cases, an administrator or user may intervene to provide a name for the mechanism as well.

In block 908, a subset of the model attributes and predetermined thresholds are associated with the causal inference.

In block 910, the causal inference, including the model attributes, predetermined thresholds, and the name generated in block 906 are stored as a biological mechanism in the biological mechanisms data store 608. The causal inference is now ready to be used in subsequent machine learning analysis by machine learning algorithm 606.

As stated above, antimicrobial resistance (AMR), is the phenomenon where infection-causing bacteria develop strains resistant to drugs. While most of the infection-causing bacteria are killed when treated with antibiotics and other anti-microbial therapies, some survive. The surviving bacteria have attributes that allow the bacteria to survive in the first place, and replicate. When these strains cause other infections, those strains are resistant to the previously-used antibiotics and/or antimicrobials. Over many evolutionary cycles, eventually the antibiotics and/or antimicrobials are ineffective against that strain of bacteria. Furthermore, the resistance factors, can sometimes be transmitted across bacterial strains, further exacerbating the problem.

The result is that health care providers must identify alternative therapies, and researchers must identify new drugs. Additionally, the speed that health care providers identify alternative therapies and the speed that researchers identify new drugs must be faster than the adaptive rate towards resistance by infection causing bacteria. Otherwise, health care providers will be fighting a battle against infection that they, and all the public, will eventually lose.

For at least these reasons, the World Health Organization (WHO) has identified AMR as a key threat to public health with a call to action, "combat drug resistance: no action today, no cure tomorrow." Despite the exigency of the situation and the relative straightforward nature of regulatory approval for antimicrobial therapies with a relatively high likelihood of success, economic pressures conspire to shift research resources away from developing the novel antimicrobials required to address the problem of AMR The costs of pre-clinical development of antimicrobials are frequently high relative to the profitability of antimicrobials. Development of "blockbuster" drugs, which usually aren't antimicrobials, are more profitable, and accordingly attract more funding with the concomitant attraction of research attention.

Accordingly, the application of automated methods has at least two benefits. First automated methods can speed the identification of alternative antimicrobial therapies and the development of new drugs. Second, automated methods can reduce the pre-clinical and development costs. Thus, application of causal inference methods to investigate antimicrobial resistance can effectively respond to the WHO's call to action.

Antimicrobial Resistance Terminology

Prior to describing causal inference-based investigation of antimicrobial resistance, it is worthwhile to define some terms. Antimicrobial Resistance (AMR) is the general term of resistance of infection-causing bacteria to an antimicrobial drug or therapy. Note there are several variants of this phenomenon.

Some bacterial strains are resistant to more than one therapy or class of therapy (a set of therapies making use of the same biological techniques or vectors to attack an infection). These are called multidrug resistant (MDR) strains. Where the strains are resistant to a relatively large number of therapies or classes of therapies, the strain is said to have extensive drug resistance (XDR). In some, mercifully few, cases, a strain may have pan-drug resistance (PDR), which is resistance to all known therapies or classes of therapies.

To understand the basis for AMR development, and potentially the basis to attack AMR trends, we will first discuss one way that health care providers conceptualize AMR. First, a health care provider is presented with a patient, and following appropriate examination and testing, a diagnosis is made. If an infection is involved, the associated disease is identified. Infections will have at least one bacterium causing the infection, and occasionally multiple bacteria. For each bacterium, there is a standard therapy. Accordingly, a health care provider will empirically treat the infection with a standard antibiotic drug(s) known to be effective against the most common strain of that bacterium while waiting for more definitive laboratory testing against potential resistance.

In some cases, the treatment is ineffective due to AMR bacteria. Put another way, the bacteria have a mechanism of resistance to the antimicrobials—and it is identifying and investigating these mechanisms of resistance that will be of concern of with the automation of causal inference-based investigation described herein. In the meantime, the health care provider will understandably attempt to provide an alternative therapy. One approach is to use a different class of therapy; in other words, use a drug that attacks the AMR bacteria in a way that avoids the mechanism of resistance. Another approach is to impede the AMR bacteria's mechanism of resistance. Laboratory testing of bacteria strains can help guide this selection of alternative antibiotics but takes time to identify these potential choices which can be problematic in situations involving rapidly progressing life-threatening illnesses.

Either way, an understanding of the AMR bacteria's mechanism of resistance and how to exploit it with therapies is key to addressing AMR in infections. Making most of the efforts that researchers take to investigate AMR therapies is precisely what gives health care provider options and resources in the race against the clock to treat infections. Table A below, is a non-comprehensive table describing examples of diseases, organisms, treatments, and resistances of AMR bacteria. Note that the resistance treatment selected is based on the specifics of the case. For example, against *Staphylococcus Aureus*, if a strain is resistant against methicillin, then vancomycin may be used as a resistance treatment. If the strain is vancomycin resistant, then most certainly an option other than vancomycin will be used as a resistance treatment.

TABLE A

| Antimicrobial Resistance | | | | | |
| --- | --- | --- | --- | --- | --- |
| Disease | Organism | Standard Treatment | Resistance | Mechanism of Resistance | Resistance Treatment |
| Urinary Tract Infections (UTI), Gastro- | *Escherichia Coli* | Location dependent (e.g., UTI vs. GI)- | 3rd gen cephalosporin resistance; Fluoroquinolone | Plasmid mediated beta-lactamases (ESBL-extended | Meropenem; tigecycline; methicillin + cefoxitin; fosfomycin; multi-Abx |

TABLE A-continued

Antimicrobial Resistance

| Disease | Organism | Standard Treatment | Resistance | Mechanism of Resistance | Resistance Treatment |
|---------|----------|--------------------|-----------|--------------------------|----------------------|
| Intestinal (GI) infections, renal infections, wound infections. Sepsis. | | BACTRIM; nitrofurantoin; fluoroquinolone; ciprofloxacin; levofloxacin; azithromycin | resistance; (multidrug resistance (MDR)) | spectrum); AmpC beta-lactamase; carbapenemases; hydrolyzing oxacillinase-48 | "cocktails" |
| Skin infections, pneumonia, surgical wounds, bone & joint infections, endocarditis. Sepsis. | Staphylococcus Aureus | Beta-lactam antibiotic | Methicillin resistance; vancomycin resistance; (multidrug resistance (MDR)) | Non-native gene encoding a penicillin-binding protein (PBP2a). Coded near mecA gene with mobile element (SCCmec), expression through sensor protein MecR1 and repressor (Mecl). | Trimethoprim-sulfamethoxazole, vancomycin, teicoplanin, clindamycin, minocycline, doxycycline, linezolid, ciprofloxacin, daptomycin |
| Pneumonia, UTIs. Sepsis. | Klebsiella Pneumoniae | Carbapenems | Carbapenem resistance; 3rd gen cephalosporin resistance; (multidrug resistance (MDR)) | Oxacillinase resistance (OXA-48); carbapenemase; biofilm | High dose meropenem, colistin, fosfomycin, tigecycline, aminoglycosides; polyenones (experimental) |
| Pneumonia, meningitis, endocarditis, otitis media. Sepsis. | Streptococcus Pneumoniae | Penicillin | Penicillin and beta-lactam resistance, also macrolides, fluoroquinolones; (multidrug resistance (MDR)) | Genetic mutations in penicillin binding protein; macrolides-alteration of 23S rRNA subunits by ermB gene; active efflux pumps | Beta-lactam antibiotics, cefuroxime, cefotaxime, ceftriaxone, vancomycin, amoxicillin/clavulanate |
| Ventilator associated pneumonia, meningitis, others. Sepsis. | Acinetobacter Baumannii | Broad spectrum cephalosporin; beta-lactam + inhibitor, carbapenems. | Carbapenem resistance; tobramycin; ciprofloxacin; polymyxins; (multidrug resistance (MDR)) | Beta-lactamases (with promoter ISAba1), altered cell wall channels, bacterial efflux pumps, mutations in gyrA, parC (quinolones), aminoglycoside-modifying enzymes | Empiric: Ceftazidime, cefepime (with beta-lactamase inhibitor-sulbactam), imipenem, meropenem, polymyxins, tetracyclines, colistin, cif |
| Cystic Fibrosis related pneumonia. Sepsis | Pseudomonas aeruginosa | Ceftazidime, ciprofloxacin; cefepime; gentamycin; aztreonam; carbapenems; ticarcilin; ureidopenicilins | Carbapenem resistance; aminoglycosides, quinolones, beta-lactams; (multidrug resistance (MDR)) | Biofilm, low membrane permeability, efflux pumps, antibiotic inactivating enzymes (beta-lactamase) | Doripenem, plazomycin; New approaches: PLO7001 (protein epitope mimetics); quorum sensing inhibition, lectins; phage therapy; nanoparticles |

Some observations are in order. Upfront a health-care provider may not know that an infection is based on an AMR bacterium. For example, initial tests may identify that a patient's pneumonia is caused by *staphylococcus* infection but might not indicate that the *staphylococcus* strain is AMR. Only on subsequent testing will the health-care provider discover that the organism is resistant to the initial therapy; this can significantly delay implementation of effective treatment, often with severe negative clinical outcomes for the patient. Thus, improved testing methodologies might allow health-care providers to apply treatments taking AMR into account much earlier.

Improved testing may be a result of combining experimental results across different areas, utilizing causal-based inference of heterogeneous data. Combining experimental results where different experiments have subjects from different geographies can detect the spread of AMR bacterial strains. Combining experimental results to determine symptoms more indicative of AMR early on even prior to bacterial testing can speed diagnosis of AMR.

An infectious disease may have multiple bacteria causing the infection, and the health care provider may not be sure as to what the actual cause is. For example, pneumonia may be either a *staphylococcus* or a *streptococcus* infection. Selection of therapies against AMR can be based on what combination of bacteria are involved in the infection.

The identification of the relationship between mechanisms of resistance of different bacteria can suggest the development of drugs that are effective across multiple AMR bacteria. Again, the combination of results of different types of experiments, utilizing causal-based inference of heterogeneous data, lends itself to such applications. Thus, experimental data against one bacterial strain can be combined with experiment data with against a different strain of a different species of bacteria altogether, to determine methods of attack against both. This can be especially important given that mechanisms of resistance can be transmitted across different bacterial species.

A bacterium may have one or more mechanisms of resistance. If one applies two drugs, each of which bypasses a particular mechanism of resistance and both are effective, then those drugs are apposite. A caregiver administering a cocktail of the two drugs may thus be confident that at least one will be effective against that AMR bacterium.

Similarly, the investigation of AMR across different species of bacteria may help identify mechanisms of resistance that are apposite to each other. In other words, it may be possible to identify using causal-based inference of heterogeneous data instances where a bacteria strain exploits one mechanism of resistance, that by virtue of using that mechanism of resistance it cannot exploit another mechanism of resistance. In other words, identifying apposite mechanisms of resistance may aid the development of cocktail therapies where it is likely that at least one of the drugs will overcome a particular strain's mechanism of resistance. In this way, short of being faced with an infection being pan-drug resistant, the health care provider may have more effective treatment options. In the meantime, researchers can focus on identifying different vectors of attack on otherwise AMR strains.

Turning back to Table A, four of the organisms, *Escherichia Coli, Klebsiella Pneumoniae, Acinetobacter Baumannii*, and *Pseudomonas Aeruginosa* are known to account for 75% of all AMR deaths. In 2020, in the United States alone, three million people were infected with AMR bacteria leading to 35,000 deaths. *Staphylococcus Aureus*, and another five, *Staphylococcus Aureus, Enterococcus Faecium, Helicobacter Pylori, Campylobacter*, Salmonellae, and *Neisseria Gonorrhoeae* are on the WHO's list for critical research and development for new Antibiotic treatments. As can be seen, there is a public need for the application of causal based investigation of AMR including the use of heterogeneous data.

Causal Inference-Based Investigation of Antimicrobial Resistance

While the discussion of causal inference thus far has been in general, we now turn applying these techniques to investigation of AMR. The following discussion will be in the context of making use of heterogeneous data sources. While the discussion makes use of the category and graph database techniques as described above, note that causal inference-based investigation of AMR may make use of other techniques as well, and the following is not to be limited solely to the use of category and graph database techniques.

Causal inference-based investigation of AMR is a matter of selection AMR-related experiments (described in further detail below), transforming the data into normalized attribute vectors 300, loading the data into a graph database according to the discussion with respect to FIG. 4, loading the data into a category database accordingly to FIG. 5. With the data thus prepared, investigations specific to AMR may then be performed as described by either extracting data models as describe with respect to FIG. 7 and performing analytics on the extracted data model, or alternatively by performing causal inference analysis as described with respect to FIG. 8.

Because of the application of both graph techniques and category techniques, we are able to define "AMR-related" in several different ways. To start off with, where experimental records in the form of normalized attribute vectors 300 are relatively proximate to each other in a graph, they are related. Accordingly, if a normalized attribute vector 300 of an AMR incident or study is proximate to a second normalized attribute vector 300 in a graph database, then the two may be related, regardless of whether the second normalized attribute vector 300 is explicitly marked as AMR.

Also, while there are many AMR clinical trials, the attack vector and drug behavior against the bacteria is expected to vary widely. Rather than performing pharmacokinetic modeling of drugs, which relates to a drug's impact of drug dosing on a patient, we can look at bacterial kinetics i.e., the ability of the bacteria to proliferate in the presence of antibiotics. Note that AMR is the ability of bacteria to thrive in the presence of effective doses of antibiotics, previously known to either inhibit bacterial growth (bacteriostatic) or kill the bacterial organism (bactericidal). By aggregating AMR clinical trials into mathematical categories by bacterial kinetic model (also usually a set of differential equations), an AMR clinical trial's normalized attribute vector 300 being in the same mathematical category as another is a form of being AMR related.

Additionally, where AMR clinical trials have their respective normalized attribute vector 300 in different categories, but where a mathematically non-trivial (non-identity) natural transformation or functor is present, those clinical trials are AMR-related.

Accordingly, there is a wide range of combinations of heterogeneous experimental data that have been underutilized in the development of novel AMR therapies that can be addressed with causal inference-based investigation of AMR. Here, development is intended to be construed broadly. Development includes aspects of evaluating new compounds de novo for potential applications as therapies, as well as evaluating compounds already applied to be a therapy for one medical condition, for another therapy for another different medical condition. Indeed, it is a characteristic of category theory that seemingly unrelated medical conditions can in fact be related as to suggest uses of the same therapy. One example is the use of anti-aging medication which originally was used solely for aging, and then applied to mitigate the effects of chemotherapy. Another example is the use of GLP1 agonist drugs, originally for treatment of diabetes, for new applications in weight loss.

Accordingly, we characterize the notion of drug development as described herein to subsume drug discovery not only for the identification of completely novel compounds, but also from hitherto unused compounds and new applications of existing available compounds. This is possible since causal inference-based investigation, for AMR, or otherwise is agnostic to whether a compound had been used in one application before or not. Upon performing a search seeking related compounds based on their pharmacokinetic (or other mathematical) model using the causal inference engine 118, the category database 116 will show that two compounds are related, solely on the basis of the respective mathematical models of the compounds. If we are seeking novel compounds de novo, we will not expect there to be a high correlation between the graph database 112 which represents the present knowledge. In other words, because we are not expecting that there has been prior use, we can reduce or eliminate any statistical weight given by the graph database 112 in the causal inference engine 118. However, if we are seeking prior applications, we would expect there to be at least some entries in the graph database 112 to reflect at least the original application of a candidate compound. At this point, we can then measure the distance in the graph database 112 (the number of nodes to traverse) until finding a node entry for the new application of the compound suggested by the category database 116, and perform subsequent analysis on the likely degree of relatedness as part of an evaluation for determining whether further experimentation or a even a trial should be considered. An example of such an evaluation is to see if other drug compounds in the new applications were seen to be relevant to the original application (in category theory, this can be represented as an adjunct). Other evaluations are to review the literature to see if the graph database 112 should be updated to conceptual relate the graph entries.

FIG. 10 is a flow chart 1000 of causal inference-based investigation specific to AMR. To do so, we correlate medical in-field data with clinical trial data. In block 1002 we take in-field medical instances of AMR, usually from patient records and convert to normal attribute form 300. In order to do so, we need to turn the patient record into something resembling a clinical trial. We can treat the patient record as a drug trial with one and only one subject. We can partially populate a record in normal attribute form 300 with diagnosis, organism or organisms of infection, initial standard treatment, alternative treatment, timing of treatments, and mortality.

Note that the patient record is not expected to contain a pharmacokinetic model or a bacterial kinetic model. However, we note that the in-field treatment is likely of a standard treatment, or a known AMR alternative treatment. As those treatments have known pharmacokinetic and bacterial kinetic models, indeed a pharmacokinetic model would have been required for regulatory drug approval, we can backfill into the respective normal attribute form 300 record with values from a known pharmacokinetic and/or kinetic model. In block 1004 we add the pharmacokinetic and bacterial kinetic models. Bacterial kinetic data, as it relates to resistance thresholds, can also be added as laboratory information as it becomes available. This is addressed in more detail with respect to FIG. 11 below.

In block 1006 we verify the patient record in normal attributed vector 300 form, for its pharmacokinetic and bacterial kinetic models. For example, where the patient record shows the timing of various therapies, we expect a response curve within a predetermined standard deviation. Where the response curve does not match the expected model (e.g., within a predetermined standard deviation), pharmacokinetic, bacterial kinetic, or otherwise, we may segregate those records for further analysis.

In block 1008, we load the verified normal attribute vector 300 for each patient record into the clinical trial data store 108.

Because of the addition of the pharmacokinetic and bacterial kinetic models, the loaded records can now be aggregated with actual experimental clinical drug trials. In block 1010 we add the normalized attribute vector 300 of AMR experiments and clinical drug trials to clinical trial data store 108. Here, the normalized attribute vectors 300 are expected to reference bacterial kinetic models as well as pharmacokinetic models.

In block 1012, the records in clinical trial data store 108 are loaded into the graph database 112 as described with respect to FIG. 4. Similarly in block 1070, the records in clinical trial data store 108 are loaded into the category database 116, as described with respect to FIG. 5.

Finally, in block 1014 a data model may be retrieved for further analytics as described with respect to FIG. 7, or as in block 1016 causal analysis may be performed as described with respect to FIG. 8.

Example use cases of such analysis are described with respect to FIGS. 11, 12, and 13 as follows.

Use Case—Identification of AMR Strain Testing

As described above, a challenge for health care providers is often that the provider discovers that an AMR bacterium is involved. Ordinarily, infectious bacteria are identified via test or screen from sample from a patient, and due to the time needed to culture the sample into a large enough bacterial colony, e.g., 24 to 48 hours, effective treatment may be delayed.

There are current trends to identify AMR bacteria from the onset. For example, there are presently tests for Methicillin Resistant *Staphylococcus Aureus* (MRSA). While typical MRSA screens take 24-48 hours, improved tests such as cobas vivoDx MRSA tests can be done in as little as five hours. As per this example, there is a need to be able to develop faster, more economical, and more effective AMR tests.

Such identification may be done by correlating experiments involving testing biological indicators which provide the basis for screening of one type of organism with another biological indicator. This may be achieved via causal based investigation of AMR. FIG. 11 is a flow chart 1100 of an example process to do so.

First, we load the system with the data to be correlated. Because the data includes patient data, data from experiments looking for biological markers not necessarily for AMR bacteria, and AMR bacterial experiments, the data is heterogeneous. In block 1102 we load data for patients with response curves (data showing what drug was administered, the dosage, and at what times, along with response to the drug) and mortality data, into the clinical trial data store 108, the graph database 112, and/or the category database 116 as described with respect to FIG. 10. In block 1104, we load data from experiments with biological markers not necessarily specific to AMR, and in block 1106, we load data from AMR bacterial experiments, both using the process described with respect to FIG. 10.

In block 1108, we correlate biological marker techniques against AMR bacterial experiments to identify marker techniques that may be effective in distinguishing AMR strains against non-AMR strains. This is achieved by extracting a data model as described with respect to FIG. 7 and performing analytics looking for correlations.

Depending on context, the time to perform the biological marker techniques loaded in block 1104 should be shorter than the deterioration and potential mortality of patients whose data were loaded with respect to block 1102. Accordingly, the results from the analytics performing the correlations in block 1108 can in block 1110 be filtered by a time limit identified from the negative clinical outcome data of the patients.

The result should be candidate test screens to distinguish AMR strains from non-AMR strains that are fast and accurate enough to respond to patients well before they are at risk of death.

It is to be emphasized that these techniques are not limited just to identification of AMR bacterial screens. Note that further iteration can help also support trend analysis. Examples include tracking AMR strains' impact to patients with particular attributes such as gender, age, or risk factors, and determining response curves. Combination with third party data such as epidemiological/geographic data enable tracking of the spread of AMR strains by locality.

Example Use Case—Identification of AMR Strain Therapies

Once an AMR bacterium has been identified, a therapy is to be administered. As described above, one difficulty is that as alternative therapies are identified, AMR bacteria can develop resistance to the alternative therapies. Accordingly, there is a constant demand for the development of new therapies.

Identification of alternative therapies may be done by correlating experiments involving testing of vectors to attack bacteria that bypass the AMR bacteria's mechanism of resistance. For example, a particular AMR bacteria strain may generate enzymes that neutralize one particular drug.

Ideally, an alternate drug whose efficacy is not impacted by those particular enzymes and has acceptable toxicity to a patient would be identified. Identification of alternative therapies may also be achieved via a causal-based investigation of AMR. FIG. 12 is a flow chart 1200 of an example process to do so.

Similarly, to FIG. 11, we first load the system with the heterogeneous data to be correlated. In block 1202 we load data about AMR clinical trials with bacterial kinetic models, mechanisms of resistance, and/or potential vectors of attack. In block 1204, we load data from biological experiments with efficacy from particular vectors of attack on bacteria. In block 1206, we load patient data. As with FIG. 11, blocks 1202, 1204, and 1206 use the process set forth with respect to FIG. 10.

The idea is to find drugs that have been tested against patients, where those drugs should be prioritized because they relate to AMR bacteria. Accordingly, in block 1208, we identify techniques from the biological experiments loaded in block 1204 that relate to AMR bacteria in clinical trials. We then filter these techniques in block 1210, to determine which techniques had the greatest positive impact of those techniques on patients infected by the AMR bacteria in those respective clinical trials.

The operations of blocks 1208 and 1210 may be initially achieved as described with respect to FIG. 7, where a data model is extracted, and analytics to find drugs that bypass mechanisms of resistance.

However, note that a mechanism of resistance constitutes a causality relationship. Therefore, we can identify candidate drugs from performing analytics causality inference by identifying bacteria that are neutralized (i.e., can no longer hurt the patient; rendered neutral or killed) from causes other than the mechanism of resistance and identifying drugs that do not cause side effects. Accordingly, in block 1212, we now identify from the drugs identified by the analytics in blocks 1208 and 1210, precisely this set of drugs.

The result should be a set of therapies that are known to have an effect on AMR bacteria. Note that without these techniques, drugs that were insufficiently effective against the targeted bacteria might have been deprioritized or disregarded. In this way, we have a way to prioritize AMR specific bacteria for testing or attack.

In FIG. 11, we described the use of machine learning analytics by extracting a data model. In FIG. 12, we described using machine learning analytics in combination with analysis of causal inference. We now turn to a use case that focuses on causal inference.

Example Use Case—Identification of Apposite Mechanisms of Resistance

One of the challenges and dangers of AMR is that because bacteria are continually evolving and adapting, researchers and health care providers are at risk of being on a never-ending treadmill of drug development. It is not enough to analyze whether a new drug is effective against a current strain of AMR bacteria. Ideally, we would understand the mechanisms of resistance, and determine whether and what relationship one mechanism of resistance has with respect to another. If one could identify independent mechanisms of resistance, and mechanisms of attacking bacteria, and correlate the two, we would hope to use the graph of causal relationships to determine strategies to attack AMR bacteria.

One such strategy is to identify apposite mechanisms of resistance. Where a bacterial strain evolves one mechanism of resistance, it gives rise to questions as to whether it makes the bacterial strain susceptible to another attack, where a bacterial strain evolves a mechanism of resistance to the second class of attack, and/or whether it makes that bacterial strain lose the first mechanism of resistance. In other words, are there mechanisms of resistance that a bacterial strain cannot both have, thereby being susceptible to a combination of drugs that will attack at least one open vector?

Identification of apposite mechanisms of resistance may also be achieved via causal based investigation of AMR. FIG. 13 is a flow chart 1300 of an example process to do so.

Figure 12:
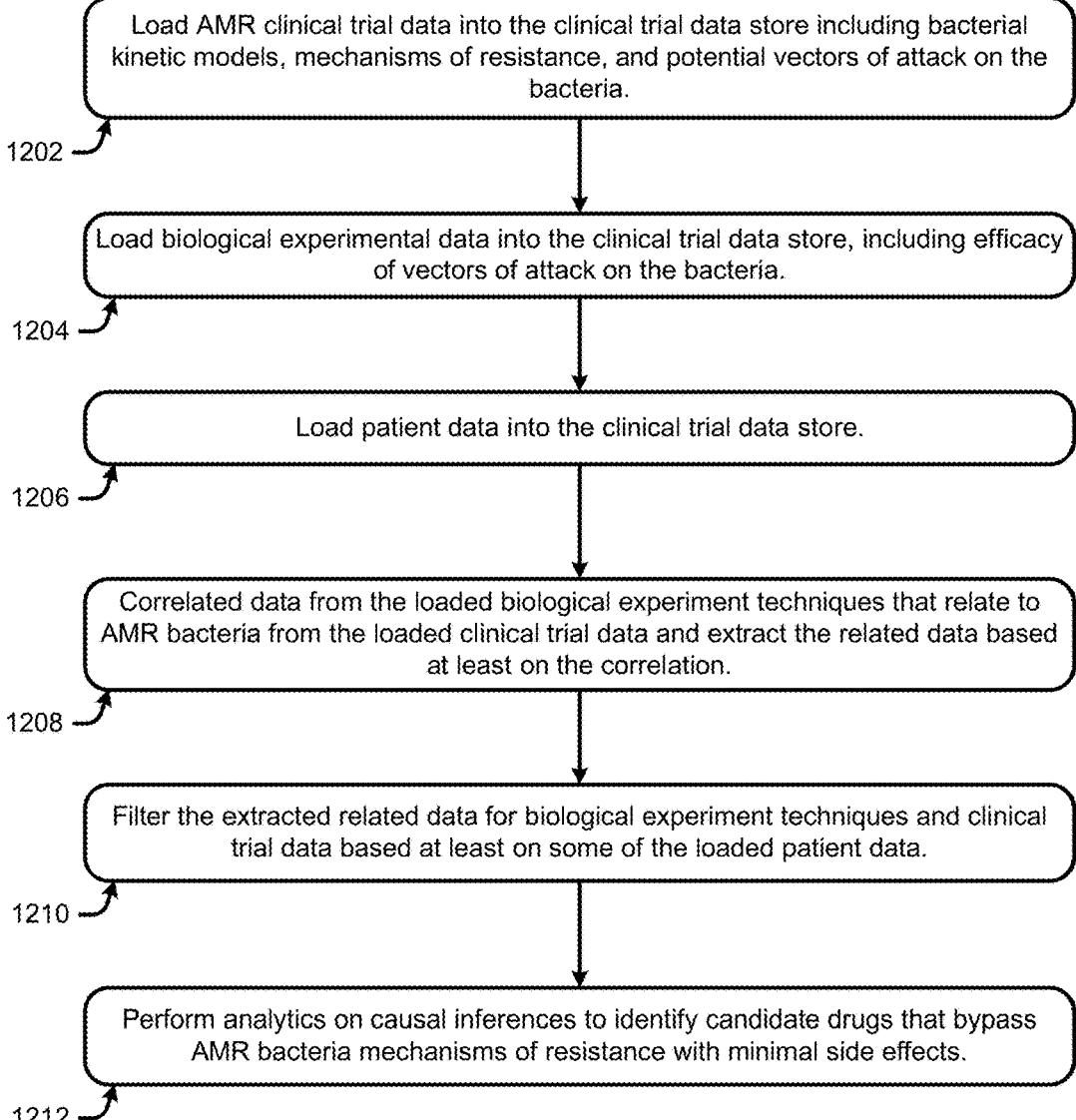
FIG. 12 is a flow chart for causal inference-based investigation of AMR with respect to identifying vectors of attack against mechanisms of resistance by AMR bacteria.

Similarly, to FIGS. 11 and 12, we first load the system with the heterogeneous data to be correlated. In block 1302, we load the system with clinical trial data containing bacterial kinetic models and data indicating the bacterial mechanism of resistance. In block 1304, we load data from biological experiments, indicating bacterial mechanisms of resistance and bacterial vulnerabilities. As the two types of data from blocks 1302 and 1304 are different, we accordingly have heterogeneous data. In block 1306 we load data from the clinical data store 108 including but not limited to data loaded via blocks 1302 and 1304 into a category database 116 and/or a graph database 112 and generate a data model. As with respect to FIGS. 11 and 12, we make use of the process set forth in FIG. 10 to load the data.

In block 1308, we are able to run causal inference queries against the data as described with respect to FIG. 8. Here, we can query for the set of therapies that are effective against one mechanism of resistance, but not another. In block 1310, we run a search for mechanisms that are apposite, also using the techniques set forth in FIG. 8.

The result will be a listing of candidate drugs, their respective efficacy against particular mechanisms of resistance, that lend themselves to clinical trials administered individually or as cocktails. An emergent property is that, with cocktails, because adaptation of a bacteria with respect to one drug in the cocktail may create a vulnerability with respect to a second drug in the cocktail, administering such a cocktail to the public at large is less likely to evolve bacteria resistant to the combination of drugs in the cocktail, and can thereby slow the AMR bacteria cycle.

Revisiting block 1310, note that as described with respect to FIG. 6, a data model 604 may be correlated to a biological mechanisms data store 608. In addition, or in the alternative, a graph database (distinct from the graph database 112) may be generated showing causality paths of both mortality and illness by a bacterium (bacterium→mortality/illness), causality paths of a drug's efficacy against bacteria (drug→bacteria), and causality paths of side effects specific to a particular class of patient (drug→side effect). Such a graph database could be used for many applications, including but not limited to identifying patterns of dependency and independence of mechanisms of resistance (which are themselves causality chains) such as apposition described above, identifying drugs that use causality mechanisms that bypass those mechanisms of resistance, and are at least less likely to trigger side effects when used.

In this way, improvement in the analysis of causal inference may be achieved beyond the techniques as described elsewhere herein. Where these techniques are implemented, not only do we have the opportunity to make AMR bacterial treatment drug discovery more economical and speedy, because we are performing analytics on the actual causality chains, we have the opportunity to attack the adaptive cycle of AMR bacteria at their core biological mechanisms. The hope would be that such a system would be able to contribute materially to WHO's call to action, "combat drug resistance: no action today, no cure tomorrow."

CONCLUSION

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method to perform causal analysis on data relating to Anti-Microbial Resistant (AMR) bacteria, comprising:

receiving patient data, clinical trial data, and bacterial kinetic model data, wherein the patient data relates to instances of AMR infections;

converting the patient data, clinical trial data, and bacterial kinetic model data into normalized attribute vectors having a normalized attribute vector form, the form being a vector format including at least a model portion that contains model attributes describing aspects of a bacterial kinetic model, an experiment portion that contains experiment attributes describing an experiment in a clinical trial, and a data portion that contains data attributes providing values representing the patient data and experimental results of the clinical trial;

loading the normalized attribute vectors into a clinical trial data store that contains data from multiple heterogeneous clinical trials, all in the normalized attribute vector format;

creating, in a graph database, a graph database instance for a set of the normalized attribute vectors stored in the data store, including:

adding, to the graph database instance, respective nodes corresponding to the normalized attribute vectors of the set; and for each of the normalized attribute vectors:

comparing the model attributes with the model attributes of normalized attribute vectors corresponding to other nodes in the graph database instance using a first similarity score;

creating respective edges in the graph database instance between nodes corresponding to compared normalized attribute vectors having a first similarity score within a first predetermined threshold;

comparing the experiment attributes with the experiment attributes of normalized attribute vectors corresponding to the other nodes in the graph database instance using a second similarity score; and creating respective edges in the graph database instance between nodes corresponding to compared normalized attribute vectors having a second similarity score within a second predetermined threshold;

creating, in a category database, a category database instance for the set of normalized attribute vectors, including, for each of the normalized attribute vectors:

comparing the model attributes to model attributes associated with categories of other normalized attribute vectors in the category database instance; and associating, in the category database instance, the normalized attribute vector with categories corresponding to model attributes of the other normalized attribute vectors in the category database instance that match the model attributes of the normalized attribute vector;

creating a causal inference model from data in the clinical trial data store, the graph database instance, and the category database instance corresponding to the normalized attribute vectors; and performing a causal analysis on the causal inference model.

2. The method of claim 1, wherein the receiving, converting, and loading are performed by a loader making use of a multi-format combinatorial parser.

3. The method of claim 2, wherein the patient data includes response curve data for a particular drug, the bacterial kinetic model data includes data about biological markers not necessarily related to AMR and time limit threshold data for the biological markers, and wherein the causal inference model is to determine whether the particular drug not currently identified as effective against AMR bacteria, is effective against AMR bacteria.

4. The method of claim 2, wherein the bacterial kinetic model data includes data about AMR mechanisms of resistance for a set of bacteria, and the clinical trial data includes vectors of attack on the set of bacteria, efficacy of the vectors of attack of a particular drug on the set of bacteria, and wherein the causal inference model is to determine whether the particular drug bypasses the AMR mechanisms of resistance of the set of bacteria and is effective on the set of bacteria.

5. The method of claim 2, wherein the bacterial kinetic model data includes data about a bacteria's mechanisms of resistance and the bacteria's vulnerabilities, the clinical trial data includes data of a first drug's efficacy against the bacteria and data of a second drug's efficacy against the bacteria, and wherein the causal inference model is to determine whether the first drug and the second drug should be combined into a cocktail where either the first drug or second drug will bypass the bacteria's mechanism of resistance.

6. The method claim 1, further comprising:

receiving a query to search for causal inferences on data in the clinical trial data store, wherein the causal analysis is performed on the created-data causal inference model in response to receiving the query.

7. The method of claim 2, wherein the multi-format combinatorial parser makes use of a machine learning model.

8. The method of claim 7, wherein the machine learning model is a large language model.

9. The method of claim 1, further comprising:

creating an empty normalized attribute form record, populating the created record with patient data, backfilling the created record with at least some data from the clinical trial data for a particular drug and at least some kinetic model data of the particular drug, and loading the created and populated record into the clinical trial data store.

10. The method of claim 9, further comprising:

checking the consistency of the created record, including:

computing the response of a patient to the particular drug based on the patient data;

comparing the computed response with a response predicted by the kinetic model data of the particular drug; and if the computed response is within a predetermined threshold of the predicted response, indicating that the created record is verified and can be loaded into the clinical trial data store.

11. The method of claim 10, wherein the predetermined threshold is a predetermined standard deviation.

12. The method of claim 1, further comprising:

creating, in the category database instance, a new category associated with the model attributes of the normalized attribute vector whose attributes fail to match the model attributes of the other normalized attribute vectors in the category database instance.

13. A system, comprising:

one or more processors; and memory including at least one computer-readable medium storing instructions that, if executed by the one or more processors, cause the one or more processors to perform causal analysis on data relating to Anti-Microbial Resistant (AMR) bacteria, the causal analysis including operations comprising:

receiving in-field patient data, clinical trial data, and bacterial kinetic model data, wherein the in-field patient data relates to instances of AMR infections;

converting the in-field patient data, clinical trial data, and bacterial kinetic model data into normalized attribute vectors having a normalized attribute vector form, the normalized attribute form being a vector format including at least a model portion that contains model attributes describing aspects of a bacterial kinetic model, an experiment portion that contains experiment attributes describing an experiment in a clinical trial, and a data portion that contains data attributes providing values representing the patient data and experimental results of the clinical trial;

loading the normalized attribute vectors into a clinical trial data store that contains data from multiple heterogeneous clinical trials, all in the normalized attribute vector format;

creating, in a graph database, a graph database instance for a set of the normalized attribute vectors stored in the data store, including:

adding, to the graph database instance, respective nodes corresponding to the normalized attribute vectors of the set; and for each of the normalized attribute vectors:

comparing the model attributes with the model attributes of normalized attribute vectors corresponding to other nodes in the graph database instance using a first similarity score;

creating respective edges in the graph database instance between nodes corresponding to compared normalized attribute vectors having a first similarity score within a first predetermined threshold;

comparing the experiment attributes with the experiment attributes of normalized attribute vectors corresponding to the other nodes in the graph database instance using a second similarity score; and creating respective edges in the graph database instance between nodes corresponding to compared normalized attribute vectors having a second similarity score within a second predetermined threshold;

creating, in a category database, a category database instance for the set of normalized attribute vectors, including, for each of the normalized attribute vectors:

comparing the model attributes to model attributes associated with categories of other normalized attribute vectors in the category database instance; and associating, in the category database instance, the normalized attribute vector with categories corresponding to model attributes of the other normalized attribute vectors in the category database instance that match the model attributes of the normalized attribute vector;

creating a causal inference model from data in the clinical trial data store, the graph database instance, and the category database instance corresponding to the normalized attribute vectors; and performing a causal analysis on the causal inference model.

14. The system of claim 13, the operations further comprising:

creating an empty normalized attribute form record, populating the created record with in-field patient data, backfilling the created record with at least some data from the clinical trial data for a particular drug and at least some kinetic model data of the particular drug, and loading the created and populated record into the clinical trial data store.

15. The system of claim 14, further comprising:

checking the consistency of the created record, including:

computing the response of a patient to the particular drug based on the in-field patient data;

comparing the computed response with a response predicted by the kinetic model data of the particular drug; and if the computed response is within a predetermined threshold of the predicted response, indicating that the created record is verified and can be loaded into the clinical trial data store.

16. A method to perform causal analysis on data relating to Anti-Microbial Resistant (AMR) bacteria, comprising:

receiving in-field patient data, clinical trial data, and bacterial kinetic model data, wherein the in-field patient data includes response curve data for a particular drug, and the bacterial kinetic model data includes data about biological markers not necessarily related to AMR and time limit threshold data for the biological markers;

converting the in-field patient data of AMR infection instances into normalized attribute vectors having a normalized attribute vector form;

backfilling the converted in-field patient data with the bacterial kinetic model data;

verifying the consistency of the backfilled in-field patient data by computing the response curve data and comparing the response curve data against the bacterial kinetic model data;

loading at least some of the backfilled in-patient data based on the verification into a clinical trial data store;

loading an experiment and the clinical trial data into the clinical trial data store;

loading a graph database and a category database with the normalized attribute vectors corresponding to the clinical trial data loaded into the clinical trial data store;

extracting from the clinical trial data store, graph database, and category database a data model based on the normalized attribute vectors for performing analytics;

performing causal analysis on the extracted data model.

* * * * *